(12) United States Patent
Bahler et al.

(10) Patent No.: US 7,887,576 B2
(45) Date of Patent: Feb. 15, 2011

(54) ENDOLUMINAL DEVICE WITH EXTRACELLULAR MATRIX MATERIAL AND METHODS

(75) Inventors: Clinton D. Bahler, Indianapolis, IN (US); Michael P. DeBruyne, Bloomington, IN (US); Neal E. Fearnot, West Lafayette, IN (US); Alan R. Leewood, Lafayette, IN (US); Jason A. Mead, Plainfield, IN (US); Thomas A. Osborne, Bloomington, IN (US); Jichao Sun, West Lafayette, IN (US); Lal Ninan, Santa Rosa, CA (US)

(73) Assignees: Cook Incorporated, Bloomington, IN (US); Cook Biotech Incorporated, West Lafayette, IN (US); MED Institute, Inc., West Lafayette, IN (US)

( * ) Notice: Subject to any disclaimer, the term of this patent is extended or adjusted under 35 U.S.C. 154(b) by 0 days.

(21) Appl. No.: 12/468,383

(22) Filed: May 19, 2009

(65) Prior Publication Data

US 2009/0248144 A1 Oct. 1, 2009

Related U.S. Application Data

(63) Continuation of application No. 11/094,021, filed on Mar. 30, 2005, now Pat. No. 7,550,004, which is a continuation-in-part of application No. 10/644,129, filed on Aug. 20, 2003, now Pat. No. 7,175,652, said application No. 11/094,021.

(60) Provisional application No. 60/404,662, filed on Aug. 20, 2002, provisional application No. 60/572,806, filed on May 20, 2004.

(51) Int. Cl.
*A61F 2/06* (2006.01)
(52) U.S. Cl. ...................... 623/1.13; 623/1.48

(58) Field of Classification Search ....... 623/1.15–1.48; 424/423
See application file for complete search history.

(56) References Cited

U.S. PATENT DOCUMENTS

| 2,127,903 | A | 8/1938 | Bowen |
| 3,562,820 | A | 2/1971 | Braun |
| 3,772,137 | A | 11/1973 | Tolliver |

(Continued)

FOREIGN PATENT DOCUMENTS

WO   WO 96/14095   5/1996

(Continued)

OTHER PUBLICATIONS

Heeschen et al., "Nicotine Stimulates Angiogenesis and Promotes Tumor Growth and Atherosclerosis," *Nature Medicine*, 7(7):833-839 (2001).

(Continued)

*Primary Examiner*—Suzette J Gherbi
(74) *Attorney, Agent, or Firm*—Brinks Hofer Gilson & Lione

(57) ABSTRACT

An endoluminal device comprises a stent and a tubular graft supported by the stent. The graft has a proximal and a distal opening and comprises a synthetic material and a bioremodelable material. The bioremodelable material is disposed on an exterior surface in at least one band adjacent at least one of the proximal and distal openings.

20 Claims, 24 Drawing Sheets

U.S. PATENT DOCUMENTS

| | | |
|---|---|---|
| 3,953,566 A | 4/1976 | Gore |
| 4,047,252 A | 9/1977 | Liebia et al. |
| 4,473,665 A | 9/1984 | Martini-Vvedensky |
| 4,502,159 A | 3/1985 | Woodroof |
| 4,517,687 A | 5/1985 | Lleblq et al. |
| 4,675,361 A | 6/1987 | Ward, Jr. |
| 4,728,328 A | 3/1988 | Hunhes et al. |
| 4,787,900 A | 11/1988 | Yannas |
| 4,842,575 A | 6/1989 | Hoffman, Jr. et al. |
| 4,861,830 A | 8/1989 | Ward, Jr. |
| 4,902,289 A | 2/1990 | Yannas |
| 4,902,508 A | 2/1990 | Badylak et al. |
| 4,956,178 A | 9/1990 | Badylak et al. |
| 5,017,664 A | 5/1991 | Grasel et al. |
| 5,024,671 A | 6/1991 | Tu et al. |
| 5,037,377 A | 8/1991 | Alonso |
| 5,108,424 A | 4/1992 | Hoffman, Jr. et al. |
| 5,160,674 A | 11/1992 | Colton et al. |
| 5,197,977 A | 3/1993 | Hoffman, Jr. et al. |
| 5,275,826 A | 1/1994 | Badylak et al. |
| 5,281,422 A | 1/1994 | Badylak et al. |
| 5,378,469 A | 1/1995 | Kemp et al. |
| 5,516,533 A | 5/1996 | Badylak et al. |
| 5,554,389 A | 9/1996 | Badylak et al. |
| 5,589,563 A | 12/1996 | Ward et al. |
| 5,693,085 A | 12/1997 | Buirge et al. |
| 5,697,969 A | 12/1997 | Schmitt et al. |
| 5,711,969 A | 1/1998 | Patel et al. |
| 5,733,337 A | 3/1998 | Carr, Jr. et al. |
| 5,755,791 A | 5/1998 | Whitson et al. |
| 5,800,510 A | 9/1998 | Schmitt |
| 5,843,158 A | 12/1998 | Lenker et al. |
| 5,851,230 A | 12/1998 | Weadock et al. |
| 5,854,382 A | 12/1998 | Loomis |
| 5,955,110 A | 9/1999 | Patel et al. |
| 5,980,799 A | 11/1999 | Martakos et al. |
| 6,004,347 A | 12/1999 | McNamara et al. |
| 6,099,557 A | 8/2000 | Schmitt |
| 6,099,567 A | 8/2000 | Badylak et al. |
| 6,162,247 A | 12/2000 | Weadock et al. |
| 6,187,039 B1 | 2/2001 | Hiles et al. |
| 6,206,931 B1 | 3/2001 | Cook et al. |
| 6,231,562 B1 | 5/2001 | Khosravi et al. |
| 6,245,099 B1 | 6/2001 | Edwin et al. |
| 6,254,627 B1 | 7/2001 | Freldbero |
| 6,264,992 B1 | 7/2001 | Voytik-Harbin et al. |
| 6,299,639 B1 | 10/2001 | Castro et al. |
| 6,334,868 B1 | 1/2002 | Ham |
| 6,358,284 B1 | 3/2002 | Fearnot et al. |
| 6,379,379 B1 | 4/2002 | Wanq |
| 6,379,710 B1 | 4/2002 | Badylak |
| 6,391,052 B2 | 5/2002 | Buirae et al. |
| 6,395,019 B2 | 5/2002 | Chobotov |
| 6,478,817 B2 | 11/2002 | Schmitt et al. |
| 6,488,705 B2 | 12/2002 | Schmitt et al. |
| 6,494,904 B1 | 12/2002 | Love |
| 6,547,814 B2 | 4/2003 | Edwin et al. |
| 6,547,815 B2 | 4/2003 | Myers |
| 6,558,414 B2 | 5/2003 | Lavne |
| 6,576,265 B1 | 6/2003 | Spievack |
| 6,579,307 B2 | 6/2003 | Sarac |
| 6,579,314 B1 | 6/2003 | Lombardi et al. |
| 6,579,538 B1 | 6/2003 | Spievack |
| 6,589,468 B1 | 7/2003 | Schmitt |
| 6,599,690 B1 | 7/2003 | Abraham et al. |
| 6,638,312 B2 | 10/2003 | Plouhar et al. |
| 6,645,242 B1 | 11/2003 | Quinn |
| 6,663,667 B2 | 12/2003 | Dehdashtian et al. |
| 6,666,892 B2 | 12/2003 | Hiles et al. |
| 6,702,848 B1 | 3/2004 | Zilla et al. |
| 6,702,849 B1 | 3/2004 | Dutta et al. |
| 6,752,826 B2 | 6/2004 | Holloway et al. |
| 7,160,318 B2 | 1/2007 | Greenberg et al. |
| 7,175,652 B2 | 2/2007 | Cook et al. |
| 7,244,444 B2 * | 7/2007 | Bates ................. 424/423 |
| 7,318,836 B2 * | 1/2008 | Brown et al. ............ 623/1.13 |
| 7,550,004 B2 * | 6/2009 | Bahler et al. ............ 623/1.13 |
| 2002/0052649 A1 | 5/2002 | Greenhalgh |
| 2002/0065552 A1 | 5/2002 | Jayaraman et al. |
| 2002/0099448 A1 | 7/2002 | Hiles et al. |
| 2002/0165601 A1 | 11/2002 | Clerk |
| 2002/0187288 A1 | 12/2002 | Lim et al. |
| 2002/0198587 A1 | 12/2002 | Greenberg et al. |
| 2003/0013989 A1 | 1/2003 | Obermiller et al. |
| 2003/0014917 A1 | 1/2003 | Rusta-Sallehy et al. |
| 2003/0021827 A1 | 1/2003 | Malaviya et al. |
| 2003/0023316 A1 | 1/2003 | Brown et al. |
| 2003/0026787 A1 | 2/2003 | Fearnot et al. |
| 2003/0032961 A1 | 2/2003 | Pelo et al. |
| 2003/0036801 A1 | 2/2003 | Schwartz et al. |
| 2003/0041386 A1 | 3/2003 | Cook et al. |
| 2003/0044444 A1 | 3/2003 | Malaviya et al. |
| 2003/0049299 A1 | 3/2003 | Malaviya et al. |
| 2003/0054022 A1 | 3/2003 | Spievack |
| 2003/0059404 A1 | 3/2003 | Spievack |
| 2003/0059405 A1 | 3/2003 | Spievack |
| 2003/0059406 A1 | 3/2003 | Spievack |
| 2003/0059407 A1 | 3/2003 | Spievack |
| 2003/0059409 A1 | 3/2003 | Spievack |
| 2003/0059410 A1 | 3/2003 | Spievack |
| 2003/0059411 A1 | 3/2003 | Spievack |
| 2003/0064111 A1 | 4/2003 | Spievack |
| 2003/0064112 A1 | 4/2003 | Spievack |
| 2003/0114917 A1 | 6/2003 | Holloway et al. |
| 2003/0133916 A1 | 7/2003 | Spievack |
| 2003/0143315 A1 | 7/2003 | Pui et al. |
| 2003/0149471 A1 | 8/2003 | Briana et al. |
| 2003/0216812 A1 | 11/2003 | Badylak |
| 2003/0232746 A1 | 12/2003 | Lamberti et al. |
| 2004/0051201 A1 | 3/2004 | Greenhalgh et al. |
| 2004/0082989 A1 | 4/2004 | Cook et al. |
| 2004/0082990 A1 | 4/2004 | Hartley |
| 2004/0146544 A1 | 7/2004 | Vyakamam et al. |
| 2004/0180042 A1 | 9/2004 | Cook et al. |
| 2005/0220848 A1 | 10/2005 | Bates |
| 2005/0273155 A1 | 12/2005 | Bahler et al. |
| 2007/0112411 A1 * | 5/2007 | Obermiller et al. ........ 623/1.13 |
| 2007/0237973 A1 * | 10/2007 | Purdy et al. ................ 428/497 |
| 2008/0312732 A1 * | 12/2008 | Hartley et al. ............ 623/1.13 |
| 2009/0048663 A1 * | 2/2009 | Greenberg ................ 623/1.35 |

FOREIGN PATENT DOCUMENTS

| | | |
|---|---|---|
| WO | WO 98/22158 | 5/1998 |
| WO | WO 98/25636 | 6/1998 |
| WO | WO 98/25637 | 6/1998 |
| WO | WO 98/26291 | 6/1998 |
| WO | WO 98/53761 | 12/1998 |
| WO | WO 01/56500 | 8/2001 |
| WO | WO 01/82836 | 11/2001 |
| WO | WO 02/15951 | 2/2002 |
| WO | WO 02/30329 | 4/2002 |
| WO | WO 03/002165 | 1/2003 |
| WO | WO 03/053287 | 7/2003 |
| WO | WO 2004/022107 | 3/2004 |
| WO | WO 2005/112821 | 12/2005 |
| WO | WO 2005/115275 | 12/2005 |

OTHER PUBLICATIONS

Johnson et al., "Matrix Metalloproteinase-9 Is Required for Adequate Angiogenic Revascularization of Ischemic Tissues, Potential Role in Capillary Branching," *Circulation Research*, 94(2):262-268 (2004).
International Standards Organization (ISO) Standard No. 10993.

The United States Pharmacopeia, The National Formulary, USP 23, NF 18 (1995).

U.S. Food and Drug Administration (FDA) blue book memorandum No. G95-1, entitled "Use of International Standard ISO-10993, Biological Evaluation of Medical Devices Part-1: Evaluation and Testing" (1995).

Hodde, "Naturally Occurring Scaffolds for Soft Tissue Repair," *Tissue Engineering*, 8(2):295-308 (2002).

Huynh et al., "Remodeling of an Acellular Collagen Graft into Physiologically Responsive Neovessel," *17 Nature Biotechnology*, 17:1083-1086 (Nov. 1999).

"USP and NF Excipients, Listed by Category," The National Formulary 23rd Edition, p. 2940-2946 (2004).

Medalie et al., ASAIO J. 42:M455 (1996).

Isch et al., "Patch Esophagoplasty Using Alloderm as a Tissue Scaffold," *J. Pediatr. Surg.*, 36(2):266-268 (2001).

Chaplin et al., "Use of Acellular Allograft for Dural Replacement; An Experimental Study," *Neurosurgery*, 45(2):320-327 (1999).

Inoue et al., "Acellular Human Dermal Matrix As a Small Vessel Substitute," *J. Reconstr. Microsurg.*, 12:307-311 (1996).

Walden et al., "Both Dermal Matrix and Epidermis Contribute to an Inhibition of Wound Contraction," *Ann. Plast. Surg.*, 45(2):162-166 (2000).

Vecchia et al., "Evaluation of Small Intestine Submucosa and Acellular Dermis As Diaphragmatic Prostheses," *J. Pediatr. Surg.*, 34(1):167-171 (1999).

Carbone et al., "Pubovaginal Sling Using Cadaveric Fascia and Bone Anchors: Disappointing Early Results," *J. Urol.*, 165:1605-1611 (2001).

Meezan et al., "A Simple, Versatile, Nondisruptive Method for the Isolation of Morphologically and Chemically Pure Basement Membranes From Several Tissues," *Life Sciences.*, 17:1721-1732 (1975).

Badylak et al., "Resorbable Bioscaffold for Esophageal Repair in a Dog Model," *J. Pediatr. Surg.*, 35(7):1097-1103 (2000).

Merguerian et al., "Acellular Bladder Matrix Allografts in the Regeneration of Functional Bladders: Evaluation of Large-Segment (>24cm$^2$) Substitution in a Porcine Model," *BJU Int.*, 85:894-898 (2000).

Wefer et al., "Time Dependent Smooth Muscle Regeneration and Maturation in a Bladder Acellular Matrix Graft: Histological Studies and In Vivo Functional Evaluation," *J. Urol.*, 165:1755-1759 (2001).

Reddy et al., "Regeneration of Functional Bladder Substitutes Using Large Segment Acellualr Matrix Allografts in a Porcine Model," *J. Urol.*, 164:936-941 (2000).

Aplin and Campbell, "The Extracellular Matrix of Human Amniotic Epithelium: Ultrastructure, Composition and Deposition," *J. Cell Sci.*, 79:119-136 (1985).

Lei et al., "Rat Amnion Type IV Collagen Composition and Metabolism: Implications for Membrane Breakdown," *Biology of Reproduction*, 60:176-182 (1999).

Meinert et al., "Proteoglycans and Hyaluronian in Human Fetal Membranes," *J. Obstet. Gynecol.*, 184(4):679-685 (2001).

Avila et al., "Reconstruction of Ocular Surface With Heterologous Limbal Epithelium and Amniotic Membrane in a Rabbit Model," *Cornea*, 20(4):414-420 (2001).

Young et al., "The Use of an Amniotic Membrane Graft to Prevent Postoperative Adhesions," *Fertility and Sterility*, 55(3):624-628 (1991).

Diethrich, "AAA Stent Grafts: Current Developments," *J. Invasive Cardiol.*,13(5):383-390 (2001).

Reference documents cited in U.S. Appl. No. 11/094,021, filed Mar. 30, 2005 (Pat 7,550,004).

Reference documents cited in U.S. Appl. No. 10/644,129, filed Aug. 20, 2003 (Pat 7,175,652).

* cited by examiner

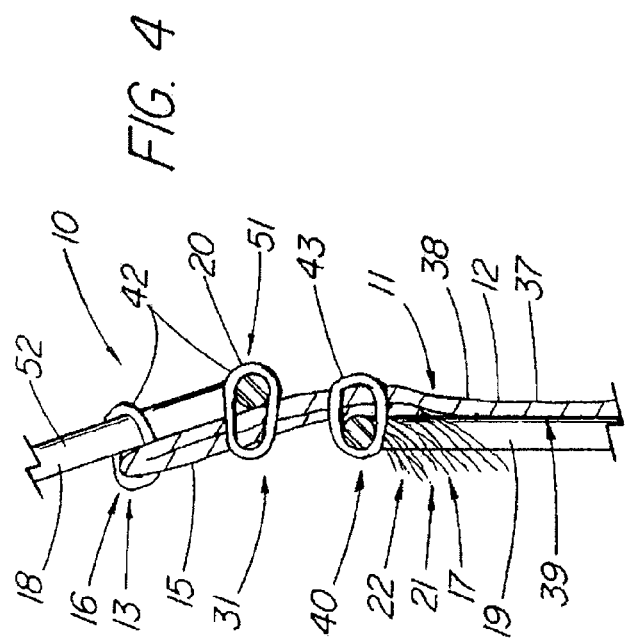
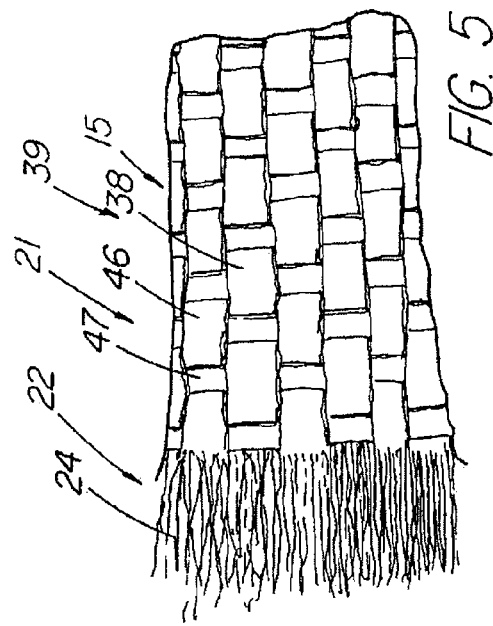
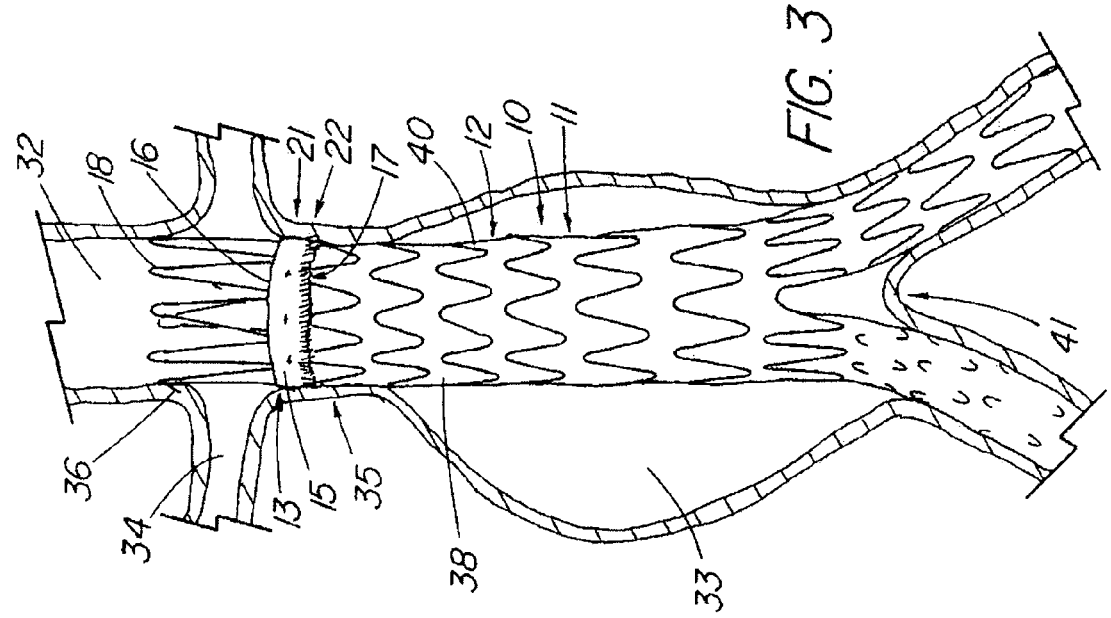

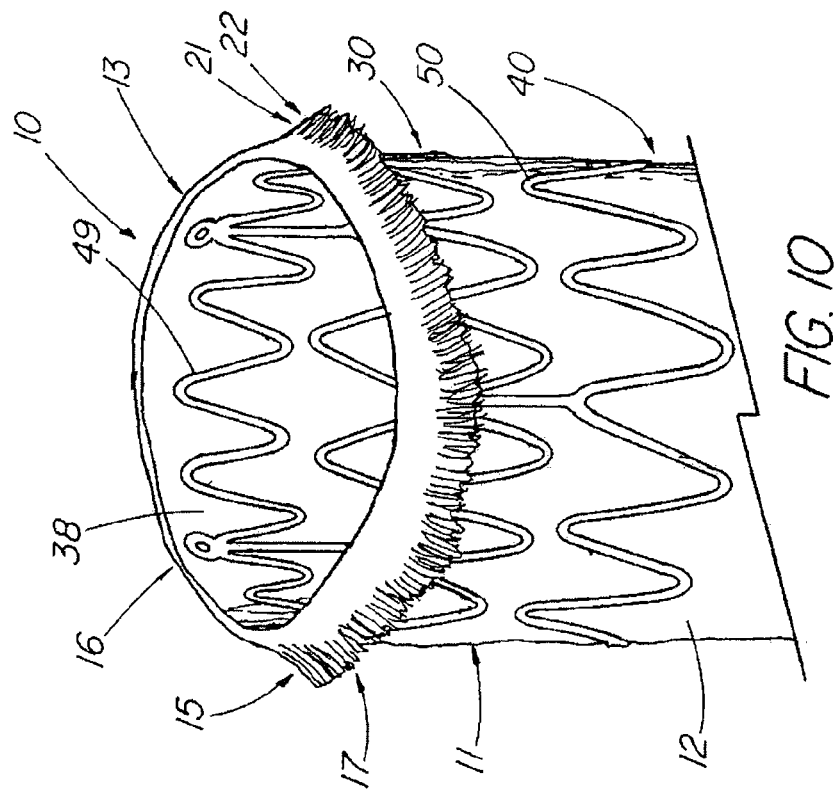
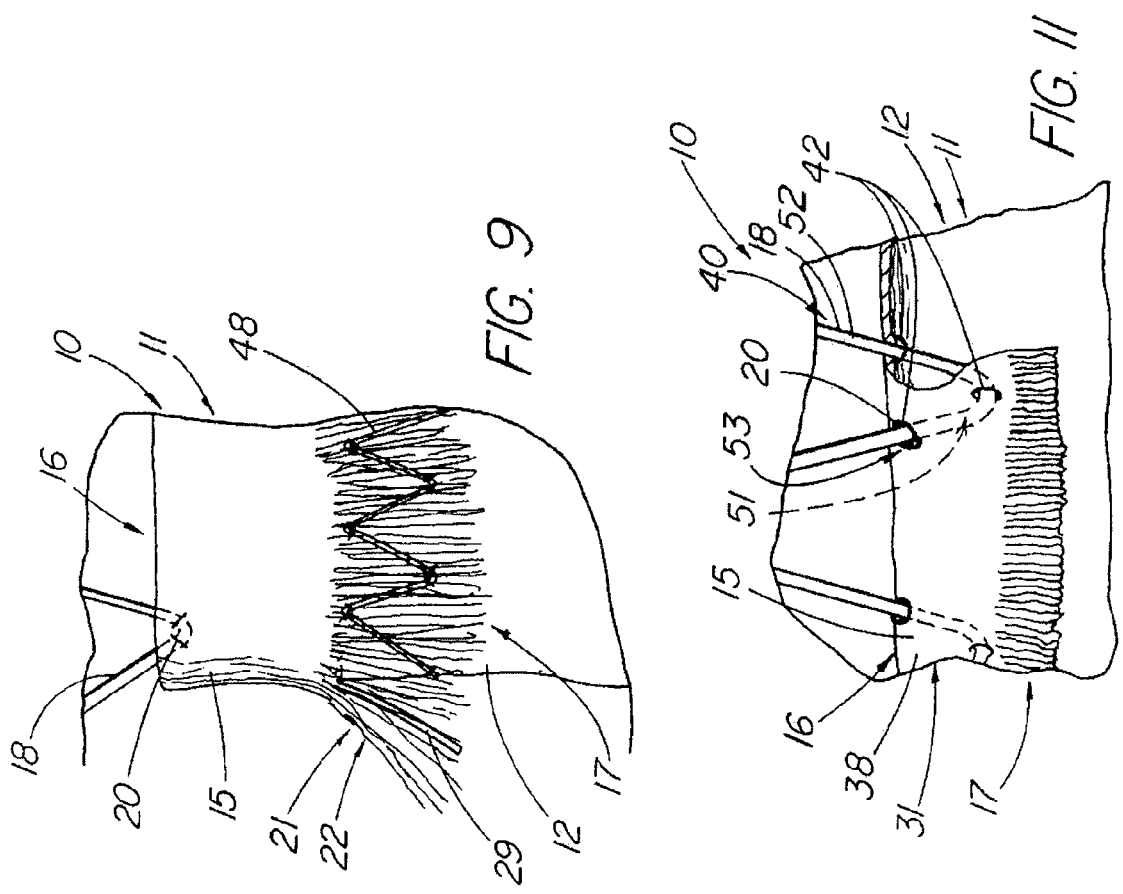
FIG. 9
FIG. 10
FIG. 11

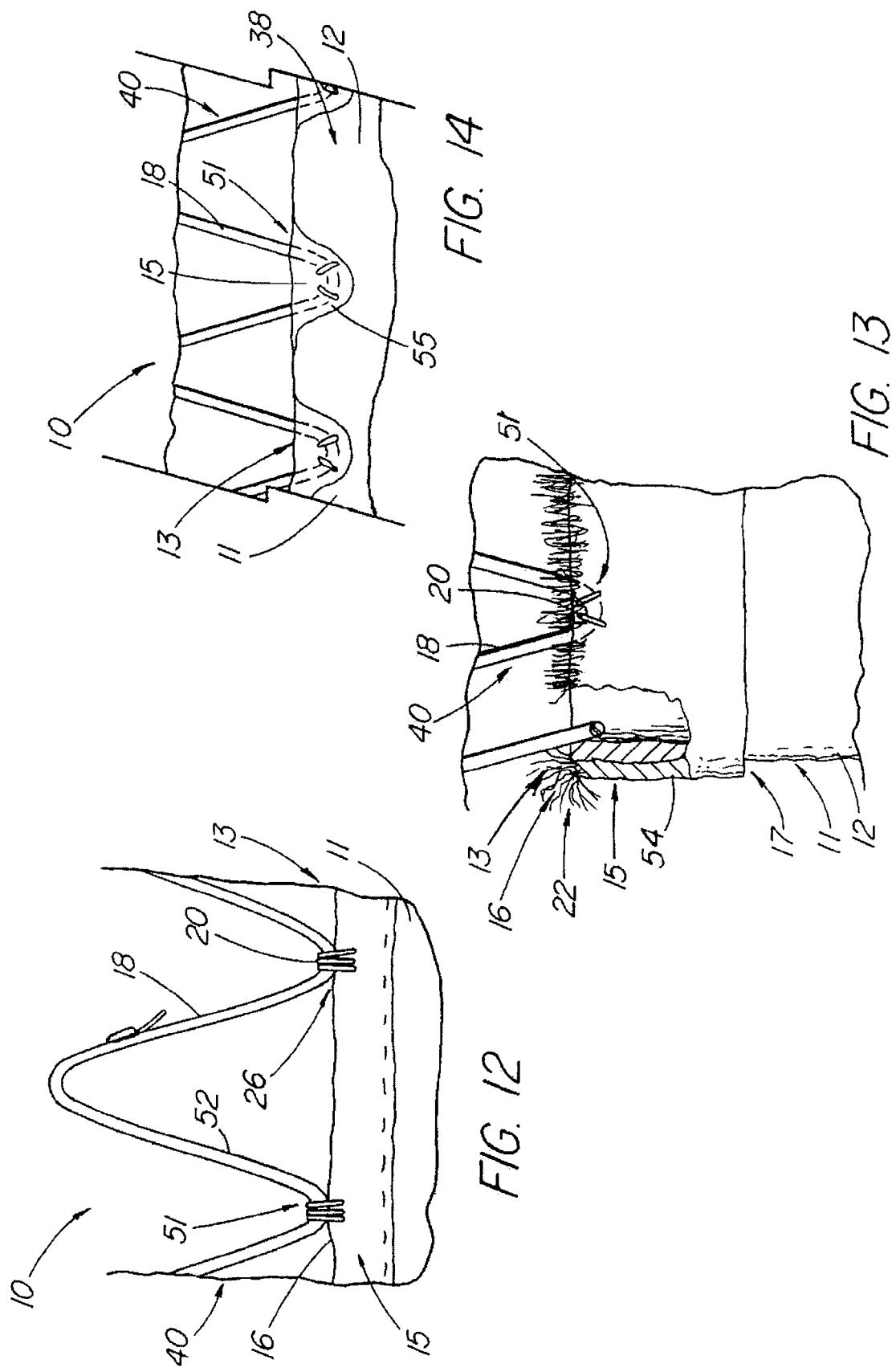

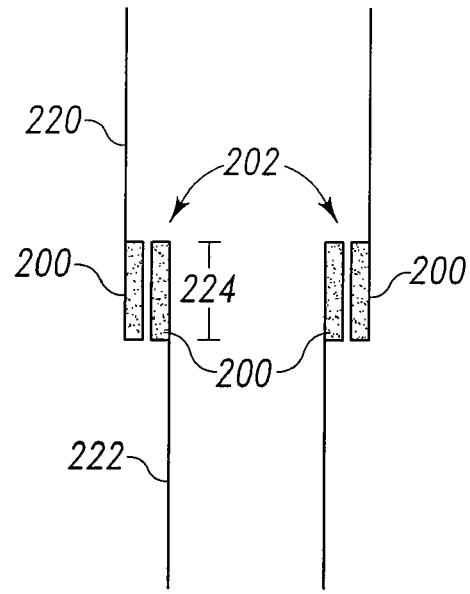
Fig. 20e
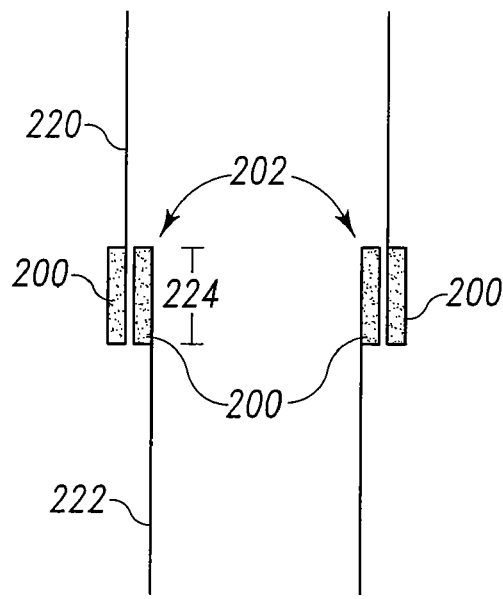 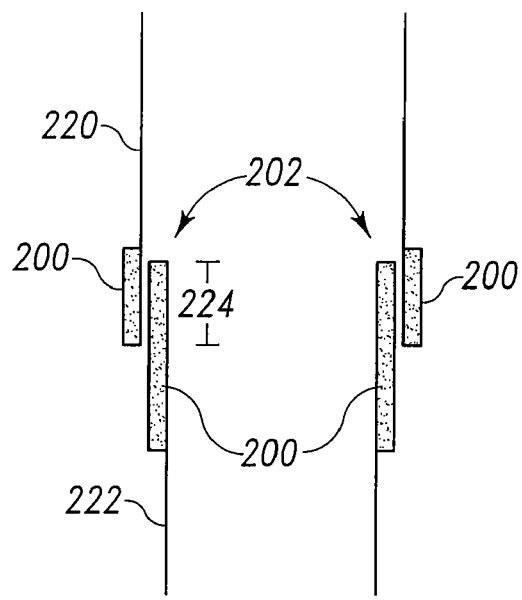
Fig. 20f Fig. 20g

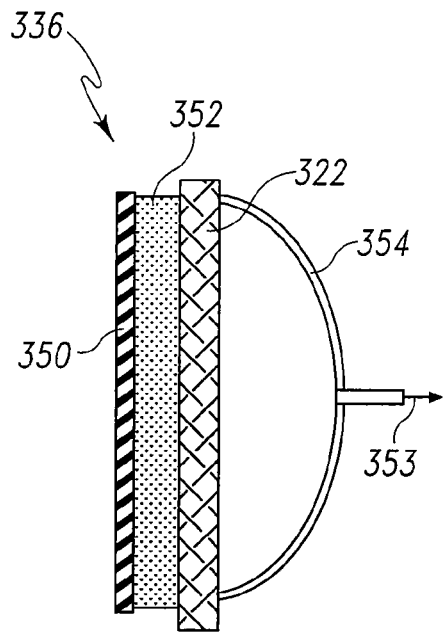
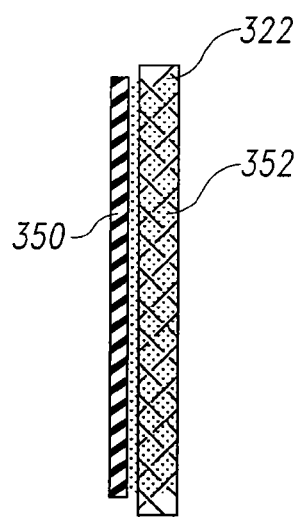
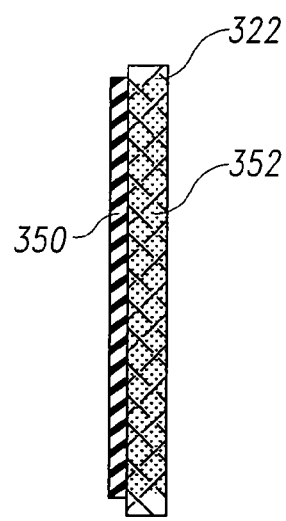
Fig. 32   Fig. 33   Fig. 34
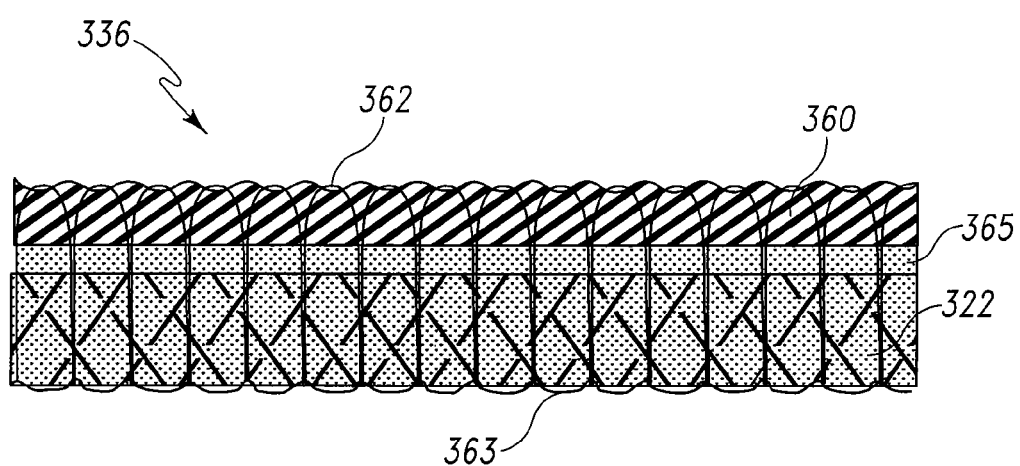
Fig. 35

ENDOLUMINAL DEVICE WITH EXTRACELLULAR MATRIX MATERIAL AND METHODS

RELATED APPLICATIONS

This application is a continuation-in-part of U.S. application Ser. No. 10/644,129, filed Aug. 20, 2003 which claims the benefit of U.S. Provisional Application Ser. No. 60/404,662, filed Aug. 20, 2002, which are incorporated herein by reference. This application also claims the benefit of U.S. Provisional Application Ser. No. 60/572,806, filed May 20, 2004, which is also incorporated by reference.

TECHNICAL FIELD

This invention relates to medical devices and more particularly, to endoluminal devices suitable for various medical applications and the methods for making and using such endoluminal devices.

BACKGROUND OF THE INVENTION

This invention will be discussed in relation to endoluminally deployed stent grafts but the invention is not so limited and can also be applied to the grafts for the human or animal body and where biological fixation is a desired or necessary function.

Throughout this specification, when discussing the application of this invention to the aorta or other blood vessels, the term "distal" with respect to an abdominal device is intended to refer to a location that is, or a portion of the device that when implanted is, further downstream with respect to blood flow; the term "distally" means in the direction of blood flow or further downstream. The term "proximal" is intended to refer to a location that is, or a portion of the device that when implanted is, further upstream with respect to blood flow; the term "proximally" means in the direction opposite to the direction of blood flow or further upstream.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study showed that in Western European and Australian men who are between 60 and 75 years of age, aortic aneurysms greater than 29 mm in diameter are found in 6.9% of the population, and those greater than 40 mm are present in 1.8% of the population.

One intervention for weakened, aneurysmal or ruptured vessels is the use of an endoluminal device or prosthesis such as a stent graft to provide some or all of the functionality of the original, healthy vessel and/or preserve any remaining vascular integrity by replacing a length of the existing vessel wall that contains the site of vessel weakness or failure. Stent grafts for endoluminal deployment are generally formed from a tube of a biocompatible material and one or more stents to maintain a lumen therethrough. Stent grafts effectively exclude the aneurysm by sealing both proximally and distally to the aneurysm, and shunting blood through its length. A device of this type can, for example, treat various arterial aneurysms, including those in the thoracic aorta, abdominal aorta, iliac, or hypogastric artery.

Two closely related aspects of stent graft function are sealing and fixation. The stent graft typically engages the wall of the lumen on both ends of the aneurysm or other defect, at proximal and distal regions referred to as landing or sealing zones. The sealing zones are typically near the termini of the stent grafts. The seal between the stent graft and the vascular wall is typically formed at these locations as a result of the circumferential apposition of the stent graft to the vascular wall. Apposition is typically maintained by the radial force exerted by stents fixed to the stent graft.

It is also desirable to fix, or anchor, the stent graft in place. For some abdominal aortic aneurysm stent grafts, proximal fixation in the neck region of the aorta is critical for long term durability of endoluminal repair. Fixation of the stent graft in part depends on mechanical anchoring mechanisms. One anchoring mechanism, the frictional forces between the stent graft and aortic wall, may be created by the interference fit between the stent graft and aorta wall. The frictional forces may be supported by an underlying stent or stents. The practice of over-sizing a device for the lumen into which it is to be placed may also increase these frictional forces. Fixation may also be assisted by small hooks or barbs that extend from the stent graft and completely penetrate the arterial wall. In both cases, fixation is immediate and does not require long term biological interaction. In contrast, tissue encapsulation may also occur in some devices over a longer time frame. Exposed stainless steel stent struts and other parts of the stent graft may eventually become completely encapsulated by tissue growth, thereby assisting fixation.

The bifurcated stent graft, one example of an endoluminal device, is known for use in treating abdominal aortic aneurysms, where the stent graft at the proximal end defines a single lumen for placement within the aorta and at the other end bifurcates into the iliac arteries. One such stent graft, disclosed in PCT application WO98/53761 is useful for repair of abdominal aortic aneurysms. That application discloses a stent graft that includes a sleeve or tube of biocompatible graft material such as woven polyester fabric or polytetrafluoroethylene (PTFE) defining a main lumen and two iliac limbs. The stent graft further includes several stents secured therealong. The stent graft is designed to span an aneurysm that extends along the aorta between the iliac and renal arteries.

In the WO98/53761 application, the fabric-covered portion of the single-lumen proximal end of the stent graft bears against the wall of the aorta above the aneurysm and distal to the renal arteries to seal off the aneurysm. Thin wire struts of a juxtarenal attachment stent traverse the renal artery ostia without occluding them. Barbs on the attachment stent help anchor the stent graft in place.

An extension module is attached to one of the limbs of the stent graft to extend through a respective iliac artery and, optionally, an iliac extension module can be connected to the other leg. The deployment of a modular stent graft into the lumen of a patient from a remote location by the use of a deployment device or introducer assembly is disclosed in the same patent application. PCT application WO98/53761 is incorporated herein by reference.

One stent graft approved by the Food and Drug Administration (FDA) to treat aortic aneurysms is the ZENITH® AAA Endovascular Graft (Cook Incorporated, Bloomington, Ind.). The ZENITH® AAA Endovascular Graft is made up of three prosthetic modules: a bifurcated main body module and two leg modules. The main body is positioned in the aorta. The legs are positioned in the iliac arteries and connect to the main body. The stent graft thus extends from a section of the aorta, typically below the renal arteries and into both iliac arteries. The graft material is made of a woven polyester fabric like that used in open surgical repair. Standard surgical suturing techniques are used to sew the graft material to a frame of stainless steel stents. These self-expanding stents provide support for the graft material.

Through the physiological process of arterial disease and aneurysm growth, both fixation and sealing may become compromised. For example, the neck of the aorta can further dilate due to disease, normal aging or the outward force of the stent. A stent graft may thereby lose its seal, thus allowing an endoleak to form. Naturally, endoleaks can be a serious problem, preventing the prosthesis from performing its function. An endoleak, even a relatively small one, may result in the aneurysm repressurizing, increasing the risk of rupture. Loss of the apposition and interference fit may also reduce the frictional forces that keep the stent graft in place. Furthermore, the fixation provided by barbs can be under risk due to the failure of the fixation barbs or local tearing of the aortic wall. Loss of fixation is highly undesirable and may also contribute to patient mortality and morbidity. For some stent grafts, loss of fixation and resulting migration may result in the occlusion of one or more blood vessels. Stent graft migration itself can cause type I endoleaks and increase the necessity for surgical intervention to repair the endoleaks.

SUMMARY OF THE INVENTION

In one aspect of the invention there is an endoluminal device that comprises a stent and a tubular graft supported by the stent. The graft has a proximal and a distal opening and comprises a synthetic material and a bioremodelable material. The bioremodelable material forms an exterior surface in at least one band adjacent at least one of the proximal and distal openings.

In another aspect of the invention there is an endoluminal device that comprises a first prosthetic module having an opening at one end and a first exterior surface. The device further comprises a bioremodelable material disposed on the first exterior surface in a first band and a second prosthetic module having an opening at one end and a second exterior surface. The first and second prosthetic modules are connected by inserting the one end of the second module into the one end of the first module to form an overlap region.

In yet another aspect of the invention there is an endoluminal device that comprises a first prosthetic module having an opening at one end, a bioremodelable material disposed within a band on the first prosthetic module, and a second prosthetic module having an opening at one end. The first and second prosthetic modules are connected by inserting the one end of the first module into the one end of the second module to form an overlap region. At least a portion of the second prosthetic module that overlaps the band is porous.

In yet another aspect of the invention there is a method of making an endoluminal device that comprises forming a graft material into a tube with a proximal and a distal opening and incorporating a bioremodelable material into the graft material so as to provide a band of bioremodelable material disposed on an exterior surface of the tube and adjacent at least one of the proximal and distal openings. The method further comprises affixing a stent so as to support the tube.

In yet another aspect of the invention there is a method of reducing endoluminal device endoleaks that comprises providing an endoluminal device comprising a tubular graft supported by a stent. The tubular graft comprises a synthetic material and a bioremodelable material. The bioremodelable material forms an exterior surface in at least one band adjacent at least one of the proximal and distal openings. The method further comprises deploying the endoluminal device into a body lumen.

BRIEF DESCRIPTION OF THE DRAWING

FIG. 3 depicts an in situ view of the embodiment of FIG. 2;

FIG. 4 depicts a cross-sectional view of the cuff of FIG. 2;

FIG. 5 depicts the free edge of the cuff portion of FIG. 2;

FIG. 9 depicts an alternative embodiment of the present invention in which the frayed portion includes additional structure to promote thrombus formation and/or tissue ingrowth;

FIG. 10 depicts an alternative embodiment of the present invention wherein the cuff portion comprises a portion of the graft material extending over the leading edge of a cannula stent;

FIG. 11 depicts a partially sectioned detail view of an alternative embodiment in which the proximal anchoring stent is attached underneath the cuff portion;

FIG. 12 depicts an enlarged side view of an alternative embodiment in which the proximal anchoring stent is attached about the edge comprising the first end of the graft material;

FIG. 13 depicts a partially sectioned side view of an alternative embodiment in which the cuff portion comprises a layer of material separate to the main body portion of the graft;

FIG. 14 depicts a side of an embodiment in which the cuff portion comprises a plurality of flaps;

FIGS. 20a-g schematically depict various locations for incorporation of ECMM relative to the interconnection between two prosthetic modules;

FIG. 32 depicts an enlarged view of a portion of the graft material showing an alternative arrangement by which ECMM can be associated with and into the graft material;

FIG. 33 depicts a second stage of the process started in FIG. 32;

FIG. 34 depicts an enlarged view of a portion of the graft material that can result from the methods of FIGS. 32 and 33;

FIG. 35 depicts an enlarged view of a portion of a graft material showing a further method by which ECMM can be impregnated into the graft material;

DETAILED DESCRIPTION

Figure 2:
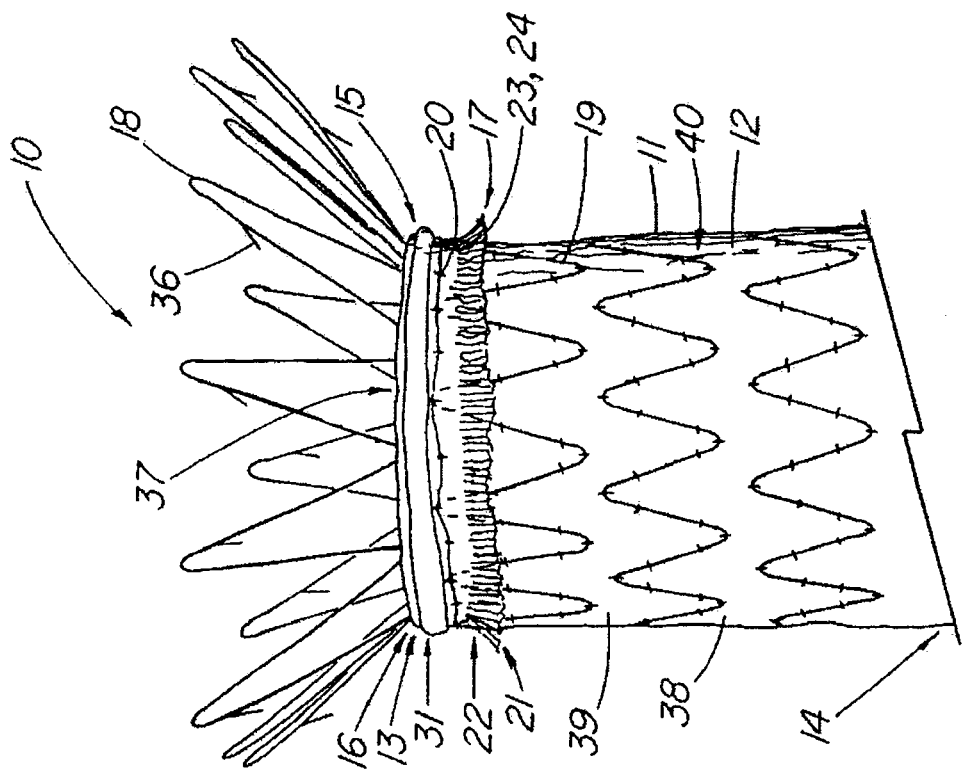
FIG. 2 depicts a side view of an embodiment of the present invention where the cuff portion includes an external sealing zone comprising a frayed portion.

For the purpose of promoting an understanding of the principles of the invention, reference will now be made to certain preferred embodiments thereof and specific language will be used to describe the same. It will nevertheless be understood that no limitation of the scope of the invention is thereby intended, any alterations, further modifications and applications of the principles of the invention as described herein being contemplated as would normally occur to one skilled in the art to which the invention relates.

In order to provide a clear and consistent understanding of this specification and these claims, the following definitions are provided.

"Bioburden" refers to the number of living microorganisms, reported in colony-forming units (CFU), found on and/or in a given amount of material. Illustrative microorganisms include bacteria, fungi and their spores.

"Disinfection" refers to a reduction in the bioburden of a material.

"Sterile" refers to a condition wherein a material has a bioburden such that the probability of having one living microorganism (CFU) on and/or in a given section of the material is about one in one-million or less.

"Pyrogen" refers to a substance which produces febrile response after introduction into a host.

"Endotoxin" refers to a particular pyrogen which is part of the cell wall of gram-negative bacteria. Endotoxin is continually shed from the bacteria.

"Purification" refers to the treatment of a material to remove one or more contaminants which occur with the material, including contaminants with which the material occurs in nature, and/or microorganisms or components thereof occurring on the material. Illustratively, the contaminants may be those known to cause toxicity, infectivity, pyrogenicity, irritation potential, reactivity, hemolytic activity, carcinogenicity and/or immunogenicity.

"Prosthesis" refers to any replacement for a body part or function of that body part. It can also mean a device that enhances or adds functionality to a physiological system.

"Prosthetic module" refers to a unit of an endoluminal prosthesis. Two or more modules can be interconnected to assemble a modular endoluminal prosthesis, such as a modular stent graft.

"Endoluminal" refers to or describes objects that can be placed inside a lumen in a human or animal body. A lumen can be an existing lumen or a lumen created by surgical intervention. This includes lumens such as blood vessels, parts of the gastrointestinal tract, ducts such as bile ducts, parts of the respiratory system, etc. "Endoluminal device" or "endoluminal prosthesis" thus describes devices that can be placed inside one of these lumens.

"Tubular" refers to the general shape of an endoluminal device which allows the device to carry fluid along a distance or fit within a tubular structure such as an artery. Tubular prosthetic modules include both branched and bifurcated modules.

"Stent" refers to any device or structure that adds rigidity, expansion force or support to a prosthesis. The stent may be coated with a polymeric film by immersion in molten polymer or any other method known to one of skill in the art.

"Stent graft" refers to a type of endoluminal prosthesis made of a tubular material and supported by at least one stent.

"Filament" refers to a long fiber. In this specification, it generally refers to a long fiber of ECMM.

"Thread" refers to a combination of filaments that are joined to form a composite strand of material suitable for weaving, sewing, or otherwise incorporating into a textile. In this specification, "thread" can refer to multiple filaments that are twisted, laid together (a zero-twist thread), knitted, woven or spun (i.e., yarn). One or more of the component filaments may be an ECMM filament, as described above "Band" refers to a circumferential region on a tubular prosthetic module. The band does not have to be of a consistent width through the circumference. The length of the band (as opposed to its circumference) is by definition shorter than the length of the endoluminal device on which it is disposed.

"Biocompatible" describes something, such as certain types of ECMM, that can be substantially non-toxic in the in vivo environment of its intended use, and is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse reaction or response. Furthermore, biocompatibility can be affected by other contaminants such as prions, surfactants, oligonucleotides, and other agents or contaminants.

"Bioremodeling" refers to the process by which a non-host matrix is processed by the physiological environment to become more like the host tissue. This process may include the production of structural collagen, vascularization, and epithelialization by the ingrowth of host cells; this may occur at a rate faster or slower than other biodegradation processes. A "bioremodelable material" is thus a material that, when implanted in a body, can be subjected to the process of and/or facilitate bioremodeling and tissue ingrowth, and does not include materials that act only as permanent scaffolds. Bioremodelable materials include polylactic acid and polyglycolic acid matrices, which may or may not be seeded with growth factors and other bioactive substances. Such synthetic matrices are described in U.S. patent application Ser. No. 09/849/141, filed May 4, 2001. Bioremodelable materials may also include other materials such as electrospun collagen (Nanomatrix, Inc., Dallas, Tex.), which may allow the ingrowth of host tissue, and facilitate the deposition of growth factors and other proteins in the bioremodeling process. Bioremodelable materials also include materials harvested from animals, such as ECMMs, which are discussed elsewhere in this application.

"Contaminant" refers to an unwanted substance on, attached to, or within, a material. This includes, but is not limited to: bioburden, endotoxins, processing agents such as antimicrobial agents, blood, blood components, viruses, DNA, RNA, spores, fragments of unwanted tissue layers, cellular debris, and mucosa.

"Extracellular matrix" is a collagen-rich substance that is found in between cells in animal tissue and serves as a structural element in tissues. It is typically a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, dura mater, liver basement membrane, pericardium or other tissues.

"Tela submucosa" or "submucosa" refers to a layer of collagen-containing connective tissue occurring under the mucosa in most parts of the alimentary, respiratory, urinary and genital tracts of animals. Tela submucosa is a preferred source of ECMM.

The apposition and fixation of an endoluminal device to the surrounding vascular wall may be improved by incorporating purified ECMM into the device where it apposes the vascular wall (i.e., at the sealing zone). This approach harnesses the ECMM's ability to improve circumferential apposition and sealing while retaining aspects of the mechanical profile of the non-ECMM device materials.

Upon implantation into a host, ECMM may undergo bioremodeling and induce the growth of endogenous tissues. ECMM may be able to serve as a matrix for, promote and/or induce the growth of endogenous tissue. Common events related to this bioremodeling process may include: widespread and rapid neovascularization, proliferation of granulation mesenchymal cells, biodegradation/resorption of implanted ECMM, and reduction of immune response.

For some vascular grafts, cellular ingrowth is important to create a seal, fix the graft in place and avoid the formation of thrombus. One of the most thrombo-resistant material known is a monolayer of endothelial cells. Without cell ingrowth or infiltration, it has been difficult to achieve a monolayer of endothelial cells using traditional graft materials. Also, without cellular ingrowth, fixation and sealing of the device is left to mechanical means, which could fail over time.

Studies have shown that warm-blooded vertebrate submucosa may be capable of inducing host tissue proliferation, bioremodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization may be observed and the submucosa material may be bioremodeled into host replacement tissue with site-specific structural and functional properties. This may occur as a result of one or more of the components of submucosa including, for example, glycosaminoglycans, glycoproteins, proteoglycans, and/or growth factors, including Transforming Growth Factor-α, Transforming Growth Factor-β, and/or Fibroblast Growth Factor 2 (basic).

ECMM can be obtained from any suitable source and can be purified in any way known to those of skill in the art. It is preferred, however, that ECMM not be antigenic or contain contaminants that render the material non-biocompatible. The other desirable characteristics of properly prepared ECMM are adequate strength, resistance to infection, resistance to excessively rapid biological degradation, non-thrombogenicity and lack of aneurysm formation.

ECMM is preferably obtained from human or other mammalian sources, including animals raised for meat production, e.g., pigs, cattle and sheep or other warm-blooded vertebrates. More specifically, ECMM is preferably made from a submucosa isolated from the alimentary, respiratory, urinary or genital tracts, renal capsule or other appropriate sources. Purified submucosa may be prepared from these tissue sources by delaminating the purified submucosa from both the smooth muscle layers and the mucosal layers. The preparation of intestinal submucosa is described in U.S. Pat. No. 4,902,508, and the preparation of tela submucosa is described in U.S. patent application Ser. No. 08/916,490, filed Aug. 22, 1997, both of which are incorporated herein by reference. The preparation of submucosa is also described in U.S. Pat. No. 5,733,337 and in 17 Nature Biotechnology 1083 (November 1999); and WIPO Publication WO 98/22158, dated 28 May 1998, which is the published application of PCT/US97/14855.

In addition to xenogenic biomaterials, autologous tissue can be harvested as well. Additionally elastin or elastin-like polypeptides (ELPs) and the like offer potential as a biologically active ECMM. Another alternative is the use of allographs such as harvested native valve tissue. Such tissue is commercially available in a cryopreserved state.

Purified tela submucosa, a preferred type of ECMM, has been previously described in U.S. Pat. Nos. 6,206,931, 6,358,284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference.

Tela submucosa, as with many animal tissues, is generally aseptic in its natural state, provided that the human or animal does not have an infection or disease. This is particularly the case since the tela submucosa is an internal layer within the alimentary, respiratory, urinary and genital tracts of animals. Accordingly, it is generally not exposed to bacteria and other cellular debris, in contrast to the epithelium of the intestinal tract and other tissues. By disinfecting the source tissue for the tela submucosa prior to delamination, the aseptic state of the tela submucosa layer can be at least substantially preserved, particularly if the delamination process occurs under sterile conditions.

In particular, it has been discovered that disinfecting the tela submucosa source tissue, followed by delaminating the tela submucosa from the tunica muscularis and the tunica mucosa, minimizes the exposure of the tela submucosa to bacteria and other contaminants. This may also minimize exposure of the isolated tela submucosa matrix to disinfectants or sterilants, if desired, thus substantially preserving the inherent biochemical profile of the tela submucosa and many of the tela submucosa's beneficial properties.

Tela submucosa tissues are preferably derived from the alimentary tract of mammals and more preferably from the small intestinal tract of pigs. A preferred source of whole small intestine is mature adult pigs weighing greater than about 450 pounds. Intestines harvested from healthy, nondiseased animals will contain blood vessels and blood supply within the intestinal tract, as well as various microbes such as E. coli contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present.

It is also desirable that ECMM be substantially free of any antibiotics, antiviral agents or any antimicrobial agents which may affect the inherent biochemical profile of the matrix and its efficacy upon implantation. One method of treating such tissue material includes rinsing the delaminated tissue in saline and soaking it in an antimicrobial agent, for example, as disclosed in U.S. Pat. No. 4,956,178, which is incorporated herein by reference. However, preferred processes avoid the use of antimicrobial agents and the like, which may affect the biochemical profile of the matrix and/or be unnecessarily introduced into the patient.

Implantable tela submucosa collagen matrix may be obtained by first disinfecting a tela submucosa source prior to removing a purified collagen matrix including the tela submucosa layer, e.g., by delaminating the tela submucosa source. Certain processing advantages as well as improved properties of the resultant tela submucosa layer may be obtained by this process, including greater ease in removing attached tissues from the submucosa layer and a low contaminant profile.

The tela submucosa source tissue (e.g., porcine small intestine) is preferably rinsed one or more times with a solvent, suitably water. The rinsing step is followed by treatment with a disinfecting agent, preferably an oxidizing agent. Preferred disinfecting agents are peroxy compounds, preferably organic peroxy compounds, and more preferably peracids. Such disinfecting agents are desirably used in a liquid medium, preferably a solution, having a pH of about 1.5 to about 10, more preferably a pH of about 2 to about 6, and most preferably a pH of about 2 to about 4. The disinfecting agent will generally be used under conditions and for a period of time which provide the recovery of purified ECMM as described herein, preferably being essentially free from pyrogens and any bioburden. Disinfection involves immersing the tissue source (e.g., by submersing or showering) in a liquid medium containing the disinfecting agent for a period of at least about 5 minutes, typically in the range of about 5 minutes to about 40 hours, and more preferably in the range of about 0.5 hours to about 5 hours.

A preferred peroxy disinfecting agent is an aqueous solution of hydrogen peroxide. The concentration of hydrogen peroxide can range from about 0.05% to about 30% by volume. The hydrogen peroxide concentration is more preferably from about 1% to about 10% by volume and most preferably from about 2% to about 5% by volume. The solution is preferably buffered to a pH from about 5 to about 9, more preferably from about 6 to about 7.5. These concentrations can be diluted in water or in an aqueous solution of about 2% to about 30% by volume alcohol (preferably ethanol). The solution temperature can range from about 15 to about 50° C. The solution temperature is more preferably from about 20 to about 40° C., most preferably from about 32 to about 37° C. The exposure time can range from about 10 to about 400 minutes, preferably from about 120 to about 240 minutes, more preferably from about 180 to about 210 minutes.

A preferred organic peroxide disinfecting agent is an aqueous solution of perpropionic acid. The concentration of perpropionic acid may range from about 0.1% to about 10% by volume, more preferably from about 0.1% to about 1.0% by volume, and most preferably from about 0.2% to about 0.5% by volume. These concentrations of perpropionic acid can be diluted in water or in an aqueous solution of about 2% to about 30% by volume alcohol (ethanol is preferred). The tela submucosa tissue source can be exposed to the organic peroxide solution for periods from about 15 minutes to about 40 hours, and more preferably in the range of about 0.5 hours to about 8 hours. Other peroxy disinfecting agents are suitable for use as described in "Peroxygen Compounds" in Disinfection, Sterilization and Preservation, 167-181 (S. Block ed., Lea & Febiger, 1991) and M. G. C. Baldry and J. A. L. Fraser "Disinfection with Peroxygens" in Industrial Biocides, 91-116 (K. Payne ed., John Wiley & Sons, 1988).

Another oxidizing disinfecting agent is an aqueous solution of chlorhexidine (1,6-di(4-chlorophenyldiguanido)hexane) in its digluconate form. The concentration of chlorhexidine digluconate may range from about 0.1% to about 15% by weight, more preferably from about 0.1% to about 2% by weight, and most preferably from about 0.2% to about 5% by weight. The solution is preferably buffered to a pH from about 5 to about 8, or more preferably from about 5.5 to about 7. These concentrations may be diluted in water or in an aqueous solution of about 2% to about 20% by volume alcohol, more preferably of about 5% to about 10%. The solution temperature may range from about 15 to about 30° C. The exposure time may range from about 10 to about 400 minutes, more preferably from about 30 to about 60 minutes. Other chlorine agents are described in G. W. Denton, "Chlorhexidine" in Disinfection, Sterilization and Preservation, 274-289 (S. Block ed., Lea & Febiger, 1991).

In preferred preparative processes, a peracid or other disinfecting agent may be dissolved in a dilute aqueous alcohol solution, wherein the alcohol has from 1 to about 6 carbon atoms, and wherein the alcohol is from about 1% to about 30% by volume of the solution. More preferred alcohols for use in the invention are selected from the group consisting of ethanol, propanols and butanols. Ethanol is the preferred alcohol for these purposes.

When a peracid is used in the disinfection, it is preferably selected from the group consisting of peracetic acid, perpropionic acid or perbenzoic acid. Peracetic acid is the preferred disinfecting agent. The peracetic acid is preferably diluted into about a 2% to about 10% by volume aqueous alcohol solution. The concentration of the peracetic acid is preferably about 0.05% by volume to about 1.0% by volume, and more preferably from about 0.1% to about 0.3% by volume. Hydrogen peroxide can also be used as a disinfecting agent.

Alternatively, or in addition, the tela submucosa tissue source may be disinfected utilizing disinfecting agents such as glutaraldehyde, formaldehyde and the like, preferably at an acidic pH. These disinfecting agents are known for their ability to introduce substantial crosslinking into collagen matrices, in contrast to the action of other disinfecting agents such as peracids which can be used to disinfect without introducing such crosslinking. Additionally, the tela submucosa source can be treated with radiation, e.g., 1-4 Mrads or more preferably 1-2.5 Mrads gamma radiation, for purposes of disinfection.

Variations on the disinfection process can also include one or more of the following:

1. Intestine is treated with 0.2% peracetic acid, 5% ethanol aqueous solution at a ratio of 10:1 solution to intestine ratio by weight. Solution has a pH of 2.6. Solution and intestine are vigorously mixed for two hours.

2. Intestine is treated with 1% peracetic acid, 25% ethanol aqueous solution at a ratio of 5:1 solution to intestine ratio by weight. Solution has a pH of 2. Solution and intestine are vigorously mixed for one hour.

3. Intestine is treated with 1% peracetic acid, 15% ethanol, and 10% hydrogen peroxide aqueous solution at a ratio of 5:1 solution to intestine ratio by weight. Solution and intestine are vigorously mixed for one hour.

4. Whole small intestine is rinsed four times with high purity water for 15 minutes. The intestine is then subjected to 1.5 Mrad Electron Beam radiation.

5. Whole small intestine is rinsed four times with high purity water for 15 minutes. Lengthwise along a conveyor belt, the intestine is subjected to high-intensity pulsed light which disinfects the intestine.

Following the treatment as described above, the tela submucosa layer is delaminated from its source, e.g., whole intestine, cow uterus and the like. It has been found that by following this post-disinfection stripping procedure, it may be easier to separate the tela submucosa layer from the attached tissues (at least from attached tunica muscularis tissue), as compared to stripping the tela submucosa layer prior to disinfection. Moreover, it has been discovered that the resultant tela submucosa layer in its most preferred form may exhibit superior histology because there is less attached tissue and debris on the surface compared to a tela submucosa layer obtained by first delaminating the tela submucosa layer from its source and then disinfecting the layer. Furthermore, the tela submucosa tissue obtained from this process may be more uniform with respect to physical and biochemical properties throughout a single tissue sample and across separate processing runs. Importantly, a highly purified, substantially sterile tela submucosa may be obtained by this process.

The stripping of the tela submucosa source is preferably carried out by utilizing a disinfected or sterile casing machine, to produce a tela submucosa which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the tela submucosa source can be employed, including, for example, delaminating by hand.

These processes may eliminate or significantly reduce contaminants contained in the tela submucosa collagen matrix. These processes may also produce a tissue that exhibits good strength and little degradation of physical and mechanical properties.

Following delamination, ECMM can be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example by chemical treatment, the matrix structure may be wrapped in a plastic or foil wrap and sterilized again using electron beam or gamma irradiation sterilization techniques.

Preferred ECMM may also be characterized by the low contaminant levels set forth in Table 1 below. The contaminant levels in Table 1 may be found individually or in any combination in a given ECMM sample. The abbreviations in Table 1 are as follows: CFU/g-colony forming units per gram; PFU/g=plaque forming units per gram; μg/mg=micrograms per milligram; ppm/kg=parts per million per kilogram.

TABLE 1

|  | First Preferred Level | Second Preferred Level | Third Preferred Level |
| --- | --- | --- | --- |
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 μg/mg | <5 μg/mg | <2 μg/mg |
| VIRUS | <500 PFU/g | <50 PFU/g | <5 PFU/g |
| PROCESSING AGENT | <100,000 ppm/kg | <1,000 ppm/kg | <100 ppm/kg |

Purified ECMM may be further processed in a number of ways to provide materials suitable for incorporation into endoluminal devices.

For example, tela submucosa tissue can also be processed to provide fluidized compositions, using techniques described in U.S. Pat. Nos. 5,275,826 and 6,264,992, which are incorporated herein by reference. In this regard, solutions or suspensions of the tela submucosa can be prepared by comminuting and/or digesting the tela submucosa with a protease (e.g., trypsin or pepsin), for a period of time sufficient to solubilize the tissue and form a substantially homogeneous solution. The submucosa starting material is desirably comminuted by tearing, cutting, grinding, shearing or the like. Grinding the submucosa in a frozen or freeze-dried state is preferred. Good results can also be obtained by subjecting a suspension of pieces of the submucosa to treatment in a high speed blender and dewatering, if necessary, by centrifuging and decanting excess waste. The comminuted tela submucosa can be freeze-dried or otherwise dried to form a powder. Thereafter, if desired, the powder can be combined with water or buffered saline or otherwise hydrated. Other pharmaceutically acceptable excipients may be added to form a fluid composition, having a preferred viscosity of about 2 to about 300,000 cps at 25° C. The higher viscosity compositions can have a gel or paste consistency.

A powder form of tela submucosa may also be produced. The tissue is first reduced to small pieces, preferably by cutting, and placed in a flat-bottom stainless steel container. Liquid nitrogen is introduced into the container to freeze the tissue, which is then comminuted while in the frozen state to form a coarse tela submucosa powder. Such processing can be carried out, for example, with a manual arbor press with a cylindrical brass ingot placed on top of the frozen specimens. The ingot serves as an interface between the specimens and the arbor of the press. Liquid nitrogen may be added periodically to the tela submucosa tissue to keep it frozen.

Other methods can be utilized to produce a tela submucosa powder. For example, tela submucosa specimens can be freeze-dried and then ground using a manual arbor press or other grinding means. Alternatively, tela submucosa can be processed in a high shear blender to produce, upon dewatering and drying, a tela submucosa powder. Further grinding of the tela submucosa powder using a prechilled mortar and pestle can be used to produce a consistent, more finely divided product. Liquid nitrogen is used as needed to maintain solid frozen particles during final grinding. Lyophilized or air-dried purified submucosa can be rehydrated with, for example, buffered saline, and used in accordance with this invention without significant loss of its biotropic and mechanical properties.

To prepare another preferred fluidized material, a tela submucosa powder can be sifted through a wire mesh, collected, and subjected to proteolytic digestion to form a substantially homogeneous solution. For example, the powder can be digested with about 1 mg/ml of pepsin (Sigma Chemical Co., St. Louis, Mo.) and about 0.1 M acetic acid, adjusted to about pH 2.5 with HCl, over about a 48 hour period at room temperature. After this treatment, the reaction medium can be neutralized with sodium hydroxide to inactivate the peptic activity. The solubilized submucosa can then be concentrated by salt precipitation of the solution and separated for further purification and/or freeze-drying to form a protease-solubilized intestinal submucosa in powder form. The tela submucosa powder can be used alone, or in combination with one or more additional bioactive agents such as physiologically compatible minerals, growth factors, antibiotics, chemotherapeutic agents, antigen, antibodies, enzymes and hormones.

Thread, yarn or fabric used in an endoluminal device may be impregnated with dry powdered or fluidized ECMM. This can be performed as the thread is spun or as the fabric is woven, or can be performed with the final tubular graft. For example, an appropriate length of synthetic thread made from polyester filaments can be incubated for a period in fluidized ECMM like that described above. When the solution has adequately penetrated or impregnated the thread, the thread can be dried. The resultant thread may be sewn or woven into a synthetic fabric as further described below. Similarly, an end of the prosthesis could be immersed in an ECMM solution to impregnate the graft material with ECMM.

It is also possible to form large surface area constructs by combining two or more tela submucosa sections using techniques described in U.S. Pat. Nos. 2,127,903 and 5,711,969, which are incorporated herein by reference. Thus, a plurality of tela submucosa strips can be fused to one another, for example by compressing overlapping areas of the strips under dehydrating conditions, to form an overall planar construct having a surface area greater than that of any one planar surface of the individual strips used to form the construct.

Variations of the above-described processing procedures may be used to produce ECMM that may be incorporated into endoluminal devices. For example, the source tissue for the tela submucosa, e.g., stomach, whole intestine, cow uterus and the like, can be partially delaminated, treated with a disinfecting or sterilizing agent followed by complete delamination of the tela submucosa. Illustratively, attached mesentery layers, and/or serosa layers of whole intestine can be removed prior to treatment with the disinfecting agent, followed by delamination of remaining attached tissues from the tela submucosa. These steps may or may not be followed by additional disinfection steps, e.g., enzymatic purification and/or nucleic acid removal. Alternatively, the tela submucosa source can be minimally treated with a disinfecting or other such agent, the tela submucosa delaminated from the tunica muscularis and tunica mucosa, followed by a complete disinfection treatment to attain the desired contaminant level (s). All such variations and modifications of this step are contemplated.

The sheets or filaments of purified submucosa can be conditioned, as described in U.S. patent application Ser. No. 08/916,490, to alter the viscoelastic properties of the purified submucosa. The purified submucosa is preferably conditioned by stretching, chemically treating, enzymatically treating or exposing the matrix structure to other environmental factors. In one embodiment, the strips of purified tela submucosa are conditioned by stretching in a longitudinal and/or lateral direction to a strain of no more than 20%. Strain is the percentage increase in the length of the material after loading.

In another embodiment, the purified submucosa is conditioned by stretching the material longitudinally to a length longer than the length of the purified submucosa from which the graft construct was formed. One method of conditioning the matrix by stretching involves application of a given load to the purified submucosa for three to five cycles. Each cycle consists of applying a load to the material for five seconds, followed by a ten second relaxation phase. Three to five cycles produces a stretch-conditioned material. The purified submucosa does not immediately return to its original size; it remains in a "stretched" dimension. Optionally, the purified submucosa can be preconditioned by stretching in the lateral dimension.

In one embodiment the purified submucosa is stretched using 50% of the predicted ultimate load. The "ultimate load" is the maximum load that can be applied to the purified submucosa without resulting in failure of the matrix structure (i.e., the break point of the tissue). Ultimate load can be predicted for a given strip of purified submucosa based on the source and thickness of the material. Accordingly, one method of conditioning the matrix structure by stretching involves application of 50% of the predicted ultimate load to the purified submucosa for three to ten cycles. Each cycle consists of applying a load to the material for five seconds, followed by a ten-second relaxation phase. The resulting conditioned purified submucosa has a resultant strain of less than 30%, more typically a strain from about 20% to about 28%. In one preferred embodiment, the conditioned purified submucosa has a strain of no more than 20%. The resultant conditioned purified submucosa strips or filaments can be used in the manner described below. The conditioning process and other relevant processes are described in U.S. Pat. No. 6,358,284 which is incorporated herein by reference.

ECMM, prepared using any variation of the processes described above, can be selectively incorporated into the endoluminal device in one or more bands that form an exterior surface of the endoluminal device. ECMM can be incorporated into the graft material by affixing the ECMM to the graft material so that the ECMM forms a separate but attached layer on the graft. ECMM may also be incorporated into the graft by integrating the ECMM into the graft material or fibers thereof. ECMM is considered to form an exterior surface of the prosthesis if the ECMM is disposed on the exterior surface, forms at least a part of an exterior surface or is partially exposed to the exterior of the prosthesis through the graft material. For example, if a band on a one-ply synthetic weave is impregnated with ECMM, it is said that ECMM forms an exterior surface of the device or the graft material.

ECMM bands are shorter than the length of the device or prosthesis, and cover less than the entire area of the synthetic graft material. The bands are preferably positioned at or near appropriate targets for fixation and/or encouraging circumferential apposition to the surrounding vessel. This selective use of ECMM in the device generally preserves many of the mechanical characteristics of the synthetic graft material, while adding the benefits of ECMM described above.

Biocompatible fabrics, non-woven materials and porous sheets may be used as the graft material. Examples of biocompatible polymers from which porous sheets can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. More preferably, the porous sheet includes a biocompatible polyurethane. Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.).

Preferably a porous polymeric sheet contains the polyurethane THORALON. As described in U.S. Patent Application Publication No. 2002/0065552 A1, incorporated herein by reference, THORALON is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A porous polymeric sheet can be formed from these two components by dissolving the base polymer and additive in a solvent such as dimethylacetamide (DMAC) and solidifying the mixture by solvent casting or by coagulation in a liquid that is a non-solvent for the base polymer and additive.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

In addition to THORALON, other polyurethane ureas may be used as a porous sheet. For example, the BPS-215 component with a MDI/PTMO mole ratio ranging from about 1.0 to about 2.5 may be used. Such polyurethane ureas preferably include a soft segment and include a hard segment formed from a diisocyanate and diamine. For example, polyurethane ureas with soft segments such as polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethylhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

In addition to polyurethane ureas, other polyurethanes, preferably those having a chain extended with diols, may be used as a porous sheet. Polyurethanes modified with cationic, anionic and aliphatic side chains may also be used. See, for example, U.S. Pat. No. 5,017,664. Polyurethanes may need to be dissolved in solvents such as dimethyl formamide, tetrahydrofuran, dimethyacetamide, dimethyl sulfoxide, or mixtures thereof.

The soft segments of these polyurethanes may contain any of the soft segments mentioned above, such as polytetramethylene oxide, polyethylene oxide, polypropylene oxide, polycarbonate, polyolefin, polysiloxane (i.e., polydimethylsiloxane), other polyether soft segments made from higher homologous series of diols, and mixtures of these soft segments. The soft segments may have amine end groups or alcohol end groups.

The hard segment may be formed from any of the diisocyanates listed above, such as 4,4'-diphenylmethane diisocyanate, tetramethylene diisocyanate, hexamethylene diisocyanate, trimethylhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The hard segment may be formed from one or more polyols. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

In addition, the polyurethanes may also be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

The porous polymeric sheet may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Patent Application Publication No. 2002/0187288 A1, which is incorporated herein by reference.

The porous polymer sheet may contain polytetrafluoroethylene or expanded polytetrafluoroethylene (ePTFE). Films or sheets of ePTFE are typically porous without the need for further processing. The structure of ePTFE can be characterized as containing nodes connected by fibrils. Porous ePTFE can be formed, for example, by blending PTFE with an organic lubricant and compressing it under relatively low pressure. Using a ram type extruder, the compressed polymer is then extruded through a die, and the lubricant is removed from the extruded polymer by drying or other extraction method. The dried material is then rapidly stretched and/or expanded at elevated temperatures. This process can provide for ePTFE having a microstructure characterized by elongated nodes interconnected by fibrils. Typically, the nodes are oriented with their elongated axis perpendicular to the direction of stretch. After stretching, the porous polymer is sintered by heating it to a temperature above its crystalline melting point while maintaining the material in its stretched condition. This can be considered as an amorphous locking process for permanently setting the microstructure in its expanded or stretched configuration. The structure and porosity of ePTFE is disclosed, for example, in U.S. Pat. Nos. 6,547,815 B2; 5,980,799; and 3,953,566; all of which are incorporated herein by reference. Structures of porous hollow fibers can be formed from PTFE, and these porous hollow fibers can be assembled to provide a cohesive porous sheet. Porous hollow fibers containing PTFE are disclosed, for example, in U.S. Pat. No. 5,024,671, which is incorporated herein by reference.

Polymers can be processed to be porous sheets using standard processing methods, including solvent-based processes such as casting, spraying and dipping, and melt extrusion processes. Extractable pore forming agents can be used during processing to produce porous sheets. Examples of extractable pore forming agents include inorganic salts such as potassium chloride (KCl) and sodium chloride (NaCl), organic salts, and polymers such as poly(ethylene glycol) (PEG) and polyvinylpyrrolidone (PVP). Pore forming agents may have a particle size from about 10 µm to about 500 µm, from about 20 µm to about 100 µm, and from about 10 µm to about 40 µm. The amount of pore forming agent relative to the polymer may be from about 20 percent by weight (wt %) to about 90 wt %, and from about 40 wt % to about 70 wt %. These sizes and amounts of pore forming agents can provide for a high degree of porosity following extraction of the pore forming agent. The porosity can be from about 20 wt % to about 90 wt %, and from about 40 wt % to about 70 wt % of the final product.

Porous sheets may be in the form of a microporous, open-celled structure in which the pores are substantially interconnected. Microporous structures can be formed by extrusion of a mixture of polymer and one or more blowing agents. Microcellular polymeric foams can be produced by exposing the polymer to super-critical CO2 under high temperature and pressure to saturate the polymer with the super-critical CO2, and then cooling the polymer. Microcellular foams can be produced as described, for example, in U.S. Pat. Nos. 4,473,665 and 5,160,674, which are incorporated herein by reference. The foaming process can be carried out on extruded polymer tube by first dissolving an inert gas such as nitrogen or CO2 under pressure into the polymer, and then forming microvoids by quickly decreasing the solubility of the gas in the polymer by changing the pressure or temperature, thus inducing thermodynamic instability. Examples of microporous polymeric structures are disclosed, for example, in U.S. Pat. No. 6,702,849 B1, which is incorporated herein by reference.

Porous THORALON can be formed by mixing the polyetherurethane urea, the surface modifying additive and a particulate substance in a solvent. Preferably the particulate is insoluble in the solvent, and the particulate may be any of a variety of different particulates or pore forming agents. For example, the solvent may be DMAC, and the particulate may be an inorganic salt. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting void-to-volume ratio can be substantially equal to the ratio of salt volume to the volume of the polymer plus the salt. The resulting pore diameter can also be substantially equal to the diameter of the salt grains.

The porous polymer sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Patent Application Publication Nos. 2003/0114917 A1 and 2003/0149471 A1, both of which are incorporated herein by reference.

ECMM can be incorporated into any kind of endoluminal device, including stent grafts and other endoluminal prostheses, for deployment into the blood vessels, biliary duct, the esophagus, or other body lumens. In particular, ECMM bands are preferably incorporated into some or all of the regions on the graft material which contact or nearly contact the surrounding vessel wall (i.e., the external sealing zones). The external sealing zones are typically near the termini of the device, although the regions can also be found in other areas such as the bifurcation of a bifurcated stent graft. The external sealing zones, however, may shift and/or change size over time and the external sealing zones can vary depending on the patient's anatomy and the particular prosthesis that is implanted. To accommodate these changes and patient-to-patient variation, it may be preferable to have ECMM bands extend beyond an approximated initial sealing zone.

Upon implantation of a prosthesis incorporating ECMM, ECMM may respond to the surrounding physiological environment in the manner described above by bioremodeling, promoting cellular infiltration, etc. ECMM itself may disappear over time, to be replaced by endogenous vascular tissue. Because ECMM is incorporated into the graft material, these responses can stimulate the surrounding tissues to meld or fuse themselves to the ECMM, and thus to the device, thereby increasing apposition and anchoring the device in place. Anchoring the prosthetic modules in this way helps prevent the modules from migrating and/or separating. Better apposition may help exclude the aneurysm, thereby preventing the build-up of hemodynamic pressure within it.

Figure 1:
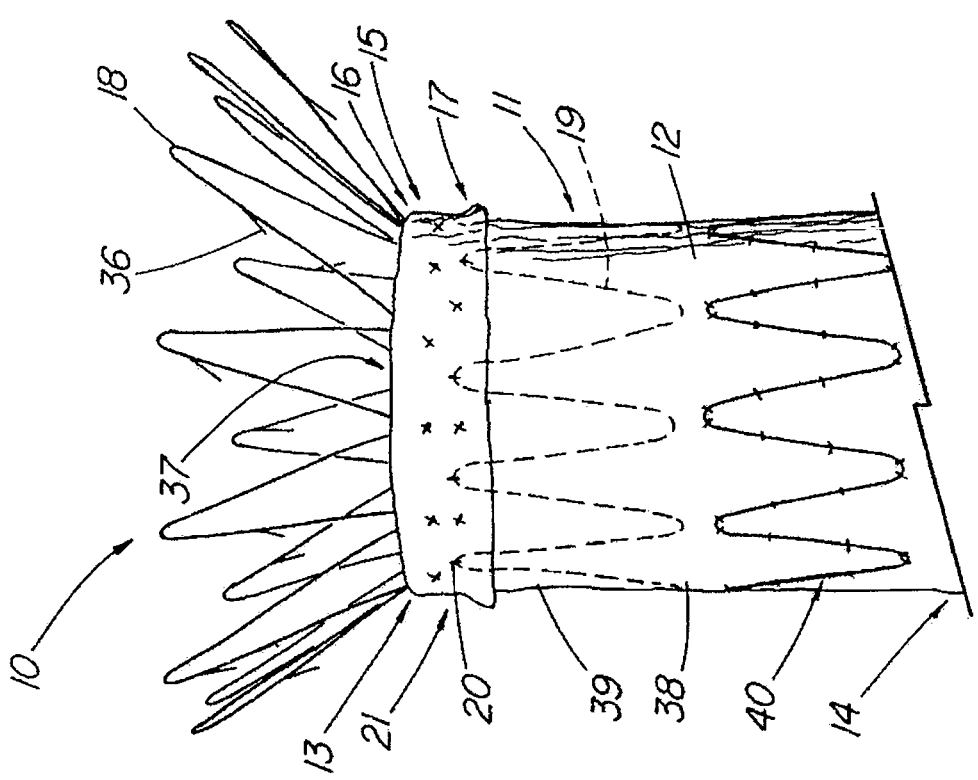
FIG. 1 depicts a side view of an illustrative embodiment of the present invention in which the graft portion includes a proximal cuff portion.

FIG. 1 depicts a graft prosthesis 10 that includes a graft portion 11 having a first end 13, which typically forms the proximal or leading edge of the main body 12 of the tubular graft portion, and a second end 14, which typically is the distal end which is further downstream from the direction of blood or fluid flow. The illustrative graft prosthesis 10 represents a modified ZENITH® AAA Endovascular Graft comprising a tubular graft portion 11 of woven polyester fiber (including a bifurcated distal portion in this embodiment to feed into the right and left iliac arteries), and a supporting structure 40 that comprises a series of zig-zag stents sewn thereto, including a proximal anchoring stent 18, such as the illustrative suprarenal zig-zag stent (or "Z stent") with barbs, extending from the proximal (caudal) end to anchor the stent graft above the aneurysmal sac.

The prosthesis 10 further includes a cuff portion 15 comprising material of the main body 12 that is folded over the outside thereof to form a double layer of material. The cuff portion 15 includes a first edge 16 or leading edge (typically a folded edge) and also comprises the first end 13 of the graft portion 11, extending distally to a second edge 17 (the free edge of the cuff). In the illustrative cuff portion 15, the free edge 17 is unattached to the main body 12 so that it is allowed to extend or flair outward to comprise a lip that serves as an external sealing zone 21 to help provide a better seal graft portion 11 and walls of the vessel in which the device is placed. It should be noted that while it may be preferable to form the cuff portion 15 by folding the excess material over upon itself, it is also within the scope of the invention for the cuff portion 15 to be a separate piece that is secured to the main body 12 of the graft portion, such that the proximal edges of the main body and cuff portions 13, 16 each comprise "cut" or free edges rather than a single folded edge. The double thickness of the cuff portion typically offers a better foundational substrate through which sutures 20 may be attached, forming knots to secure or anchor stents or other framework of the graft prosthesis 10. The length of the cuff 15 depends largely on the specific clinical application and size of the prosthesis, but preferably the free edge 17 does not extend more than a few centimeters from the first end 13, especially in an endovascular stent graft where the seal must be safely proximal of the aneurysm being excluded. The cuff portion 15, however, may extend any length, including the entire length of the main body portion 12, particularly if it is not utilized as an external sealing zone 21. Although it is generally preferred that the cuff be folded or placed over the outer surface of the main body portion 12 so as not to interfere with blood flood and promote formation of thrombus, it may be folded inward and attached, particularly if the free edge 17 can be attached or bonded in a manner that does not interrupt blood flow.

FIG. 14 depicts an alternative embodiment of the cuff portion 15 in which the cuff is configured as a series of discontinuous flaps 55 distributed around the outer perimeter of the main body portion 12 of the graft. The flaps 55 are spaced to correspond to the attachment points of the bends 51 of the anchoring stent 18. Although the illustrative embodiments each depict a suprarenal anchoring stent 18, it is not necessary to the invention that the supporting structure 40 attached to the cuff 15 comprise an anchoring stent extending from the proximal end 13 of the graft 11.

The illustrative ZENITH® AAA Endovascular Graft represents but one exemplary embodiment of the present invention. As such, the stent graft material 11 and supporting structure 40 may include other well-known designs and graft materials described herein.

The suture 20 used to attached supporting structure 40 to the graft material 11 may be made of any biocompatible fiber suitable for the application, including but not limited to, monofilament or braided multi-filament polyester, nylon, polyaramid, polypropylene, and polyethylene. Braided polyester 4-0 suture material is preferred for attaching internal stents to grafts, while monofilament suture material is preferred for attaching top stents to grafts. The polyester 4-0 suture material is nonabsorbable and has limits of 0.150 to 0.199 mm (metric size 1.5). This well-known material is commercially available from a number of companies. The suture material may be attached to a hollow needle used to thread the suture through the graft, thus attaching the stent to the graft using any suitable type of knot. It is not necessary to the invention that fiber suture be used to attach the supporting structure to the graft material. Wire, staples, clips, bonding agents, or other methods also may be used to achieve a secure attachment of the graft material and stents.

To further enhance the sealing properties of the external sealing zone 21, the free edge may be modified to increase its ability to conform to the vessel, promote thrombus formation, and/or encourage tissue ingrowth into the graft material. FIG. 2 depicts an embodiment of the present invention in which the cuff 15 includes a frayed portion 22 located about the free end 17 thereof, the frayed portion 22 comprising about 5 mm of threads and fibers (of an approximately 10 mm cuff) that have been at least partially separated from one another or unraveled such that they extend outward from the main graft body 12 and circumferentially therearound. Alternatively, the frayed portion 22 may extend the entire length of the cuff portion 15. The frayed portion 22 is particularly well adapted to making contact with the vessel and allowing thrombocytes to collect and tissue to grow thereinto, thus improving the efficacy of the seal. FIG. 3 depicts the illustrative embodiment of FIG. 2 deployed in an abdominal aorta 32 to exclude an aneurysm 33 that has formed below the renal arteries 34, usually above or at the iliac bifurcation 41. The external sealing zone 21 comprising the frayed portion 22 is positioned within the neck 35 of the aneurysm 33 where it helps the stent graft 10 seal against the healthy aortic wall tissue so that an endoleak does not occur around the proximal end 16 of the graft. The proximal anchoring stent 18 is placed across the renal arteries where it is anchored to the vessel 32 by a plurality of barbs 36. In other embodiments, the proximal anchoring stent 18 may include hooks or other structure that extend beyond or through the graft material 38 to engage the vessel and help anchor the prosthesis in place. The external sealing zone 21 may also include ECMM, as described below.

FIG. 4 depicts a cross-sectional view taken about the proximal end 16 of the graft portion 11, including the cuff portion 15 and proximal anchoring stent 18. The proximal anchoring stent 18 is attached to the inner surface 37 of the graft material 38 and secured with sutures 20 that are passed through both the main graft body 12 (inner) and the cuff portion 15 (outer) layers of material 38, preferably through the proximal or anchoring portion 31 of the cuff portion 15. In particular, a series of interconnecting (running) or separate sutures 42 anchor the proximal anchoring stent 18 to the cuff portion 15 at the bends 51 and struts 52 of the stent 18, the later being sutured about the proximal or folded edge 16 of the cuff. Additionally, the first adjacent supporting stent 19 is attached to the outer surface 39 of the main graft body 12 with another series of sutures 43. The illustrative example depicts the frayed portion 22 extending through and around the struts to minimize direct contact of the stent with the vessel wall, thus resulting in a better seal than would otherwise be possible with an externally placed stent.

FIG. 11 depicts an alternative embodiment of the present invention in which the proximal anchoring stent 18 is attached to the graft portion 11 between the main body 12 and cuff portion 15, such that the bends 51 and distal portions of the struts 52 being sandwiched between graft material 38, providing a more secure anchoring of the stent. One skilled in the medical arts would appreciate that there are multiple methods of forming the embodiment of FIG. 11. One method is to feed an end of an unassembled proximal anchoring stent through a series of holes 53 formed through the graft material until all of the bends 51 are looped underneath the cuff portion 15, as shown. The stent 18 is then joined together with cannula and solder, spot or laser welding, etc., and secured with a series of sutures 42. The illustrative method of attachment provides a backup means of preventing the proximal anchoring stent 18 from completely detaching from the graft portion 11 in the event of suture 20 failure.

FIG. 12 depicts an embodiment in which the proximal anchoring stent 18 is attached at the proximal (folded) edge 16 of the cuff portion 15 by a plurality of sutures 20 (either multiple sutures or multiple loops of a single suture) such that no portion of the bends 51 or struts overlaps with the stent graft material 11. This advantageously reduces the profile of the graft prosthesis 10 during the loading process.

While the cuff portion 15 of the illustrative embodiments is shown as a free edge 17 that is folded over itself (the tubular prosthesis 12) to create a double thickness of material (new folded leading edge 16), it is within the scope of the invention for the cuff portion to be a separate element that is attached to the main body 12 of the graft (FIG. 13), such as when the sutures 20 penetrated both layers to attach the anchoring stent 18 or other supporting structure 40. Adhesives, laser/thermal bonding, or other methods may be used supplement or achieve attachment of the two layers of material 12, 15. The separate ring-like outer cuff portion 54 comprising the outer portion of the cuff 15 preferably incorporates ECMM. Furthermore, the separate outer cuff portion 54 can comprise a material, such as a polymer that is printed, sprayed, painted, dipped, or otherwise applied to the surface of the graft prosthesis to improve the attachment between stent and graft material.

The illustrative embodiment of FIG. 13 further includes a frayed portion 22 located at the leading edge 16 of the cuff portion 15 to facilitate sealing thereat. Alternatively, the optional frayed portion 22 may be located at the second edge 17 of the cuff 15, similar to the embodiment of FIG. 2, or it may be located at the first edge 13 of the main body 12, or any combination of the three free edges 13, 16, 17. By being separate pieces, the outer cuff or band portion 54 and main body may be used to form a sandwich of material to secure the anchoring stent 18 therebetween (not shown), similar to the embodiment of FIG. 11. Although the illustrative separate outer cuff 54 completely encircles the main body 12 to which it is attached, it may be divided into discrete sections that are located at the attachment points of the stent bends 51 to provide a double thickness of material.

FIG. 5 depicts an enlarged view of the frayed portion 22 and how it is formed from material 38 of the cuff portion 15. The illustrative TWILLWEAVE® graft material 38 (Selzer-Vascutek Ltd., Inchinnan, Scotland, UK) comprises a woven polyester fabric which is frayed by separating the longitudinal threads 46 from one another and from the cross threads 47 with which they are interwoven. Once the ends 23 of the threads 46 are separated, typically using a tool or machine suitable for creating a frayed portion 22 of the desired length, the fibers 24 that comprise the individual longitudinal threads 46 are preferably, but not necessarily, also unraveled and separated from one another, allowing the frayed portion 22 to assume a "fuzzier" configuration that enhances the sealing properties of the external sealing zone 21 and provides an improved substrate for tissue ingrowth. Generally, it is preferred that the portion in which the fibers 24 are separated from one another, comprises at least a substantial portion of the frayed portion 22. The length of frayed portion 22 of a typical stent graft comprises at least 2 cm of the cuff portion 15 (preferably 5 mm or more).

Figure 6:
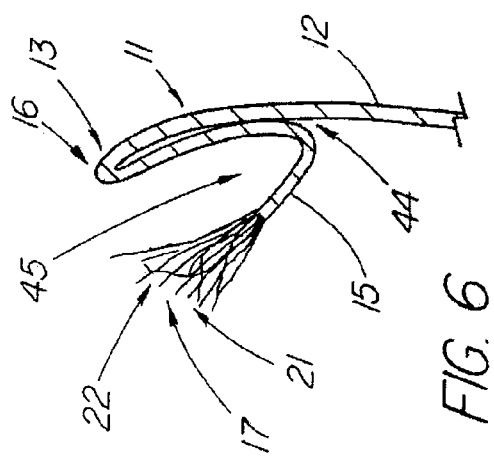
FIG. 6 depicts a cross-sectional embodiment of the present invention wherein the free edge of the cuff portion is directed toward the first end of the graft.

FIG. 6 depicts an embodiment in which the external sealing zone 21, including the illustrative frayed portion 22, is configured such that the free edge 17 of the cuff portion 15 is directed proximally (toward the first or folded edge 16), to produce a fold 44 that creates gutter-like pocket 45 that is able to collect any blood passing around the leading edge 16 of the graft 11 to prevent an endoleak and promote thrombus formation. The pocket 45 can be created by any means known to those in the medical arts, including treating and forming the cuff material using a chemical agent, heat, etc. such that it can maintain such a shape; or by adding wires or other supporting structure (not shown) that reshapes the cuff portion 15 into the illustrative pocket 45 configuration.

Figure 7:
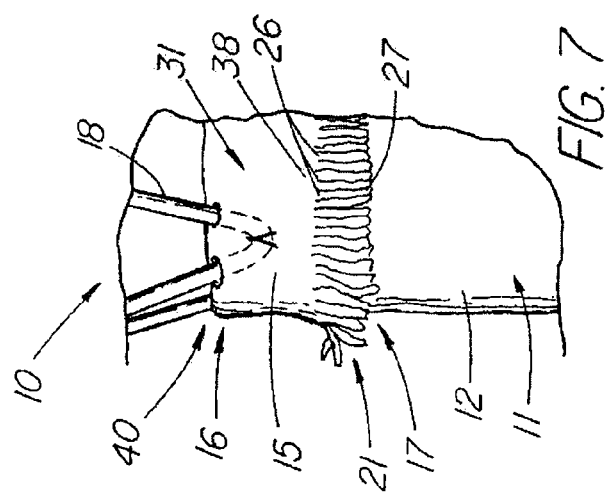
FIG. 7 depicts an alternative cuff embodiment wherein a fringe is cut into the free edge of the graft material.

Although woven polyester fiber and other selected fabrics usable in medical applications are generally able to be unraveled to create a frayed portion 22, some fabrics and unwoven materials potentially suitable for medical applications, such as polymer sleeves, biomaterials, etc., cannot be frayed in the same manner. FIG. 7 depicts an external sealing zone 21 created a series of closely adjacent cuts 26 or slices through the material to form fringe elements 27 about the free edge 17 of the material. The length, width, and configuration of the fringe elements 27 (fringed portion) are largely determined by the clinical application and type of material 38 comprising the cuff portion 15.

Figure 8:
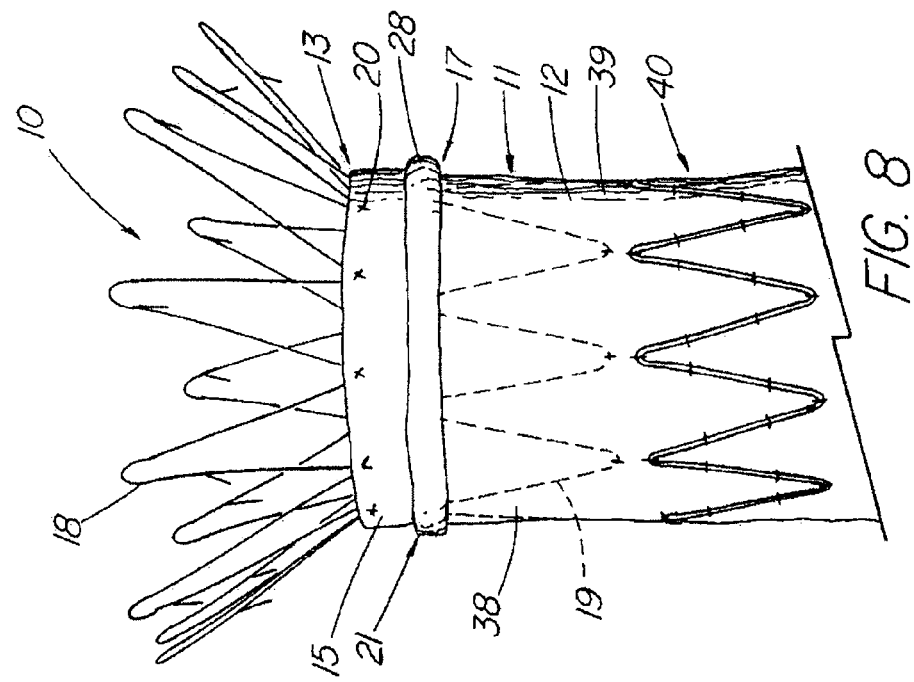
FIG. 8 depicts an alternative embodiment of the present invention wherein the external sealing zone comprises a band of extracellular matrix material ("ECMM") attached to the graft.

In addition to the external sealing zone 21 comprising the free edge 17 of the cuff portion 15, as with each of the embodiments described above, FIG. 8 depicts an embodiment wherein the external sealing zone 21 comprises a band 28 of separate material such as another suitable biocompatible material including the ECMM described above and configuration which is attached to the outer surface 39 of the graft. Such materials should be effective for creating a seal with the vessel wall and/or encouraging cell ingrowth. Such a band of material 28 can be affixed over the cuff portion 15, such as over the free edge 17, as shown, attached below the cuff 15 to further take advantage of the free edge 17 for sealing, or the cuff portion 15 may be eliminated entirely if not needed for additional anchoring support. While the illustrative embodiment depicts an external sealing zone 21 where a frayed portion 22 encircles the graft 11 in a ring-like manner, the sealing zone may assume other configurations, such as helically or serpentine shaped strips of material, discrete staggered patches of material/fringe, etc.

The external sealing zone 21 may be augmented with additional structure, materials, or agents that further enhance its sealing properties. One example includes tissue-engaging elements 29, such as the illustrative barbs depicted in FIG. 9. The barbs 29 may be configured to help anchor the graft prosthesis 10 in the vessel, or their primary function may be limited to providing irritation or trauma to the vessel wall for stimulating cell proliferation into the external sealing zone 21. The tissue-engaging elements 29 may comprise any suitable structure, such as a plurality of small diameter wires, which are interwoven into the cuff portion 15, or attached in any suitable manner, such as the illustrative method in which the barbs 29 originate from a common basal element 48 that encircles the graft portion 11 and is designed to be collapsible (e.g., a zig-zag shaped element). The tissue-engaging elements 29 may also be configured to bias the cuff portion toward the wall during delivery (e.g., by adding springs or other biasing mechanisms about the common basal element 48). For example, the prosthesis 10 may be loaded such that the cuff portion extends proximally from the main body portion 12. As the graft prosthesis is unsheathed for delivery, the embedded elements 29 spring back and flip the cuff portion distally to engage the walls of the vessel. This has the advantage of eliminating the extra thickness of the cuff portion 15 during loading, yet retaining the advantages it provides following deployment.

Besides tissue-engaging structures 29, the external sealing zone 21 may be impregnated with a bioactive or pharmacological agent that enhances sealing properties, such as a thrombin or ECMM powder, or another agent for stimulating thrombus formation about the external sealing zone 21. Other possible materials or agents include, but are not limited to, growth factors or biomaterials for stimulating tissue ingrowth, materials that swell in the presence of blood, or other substances that help form a physical barrier to fluids.

FIG. 10 depicts an embodiment of the present invention in which the cuff portion 15 extends beyond and over a self-expanding or balloon-expandable outer stent 50 and whose function is primarily to serve as an external sealing zone 21, rather than also being a substrate for attachment of a proximal anchoring stent or other supporting structure 40. In the illustrative example, which depicts a cannula-type stent 30, such as the illustrative ZILVER® Stent (Cook Incorporated, Bloomington, Ind.), the cuff portion 15 comprising the frayed portion 22, extends a few millimeters beyond the proximal or first end 13 of the stent and is unattached to the stent 50, although it optionally might include a series of sutures above the frayed portion 22 to maintain a folded edge 16 and prevent the cuff portion from inverting. In the illustrative example, the prosthesis 10 includes an inner stent 49 to form a sandwich configuration in which the two stents 49, 50, one expanding slightly larger than the other, engage and maintain the graft material 38 therebetween, thereby eliminating the need for suturing the graft portion 11 to the supporting structure 40. It is certainly within the scope of the invention, however, for either stent to be eliminated and have the graft material sewn or otherwise attached to the stent supporting structure 40 in a manner similar to other depicted embodiments. Additionally, other types of cannula or non-cannula stents can be substituted for the illustrative stents 49, 50, which need not be the same as one another.

Figure 15:
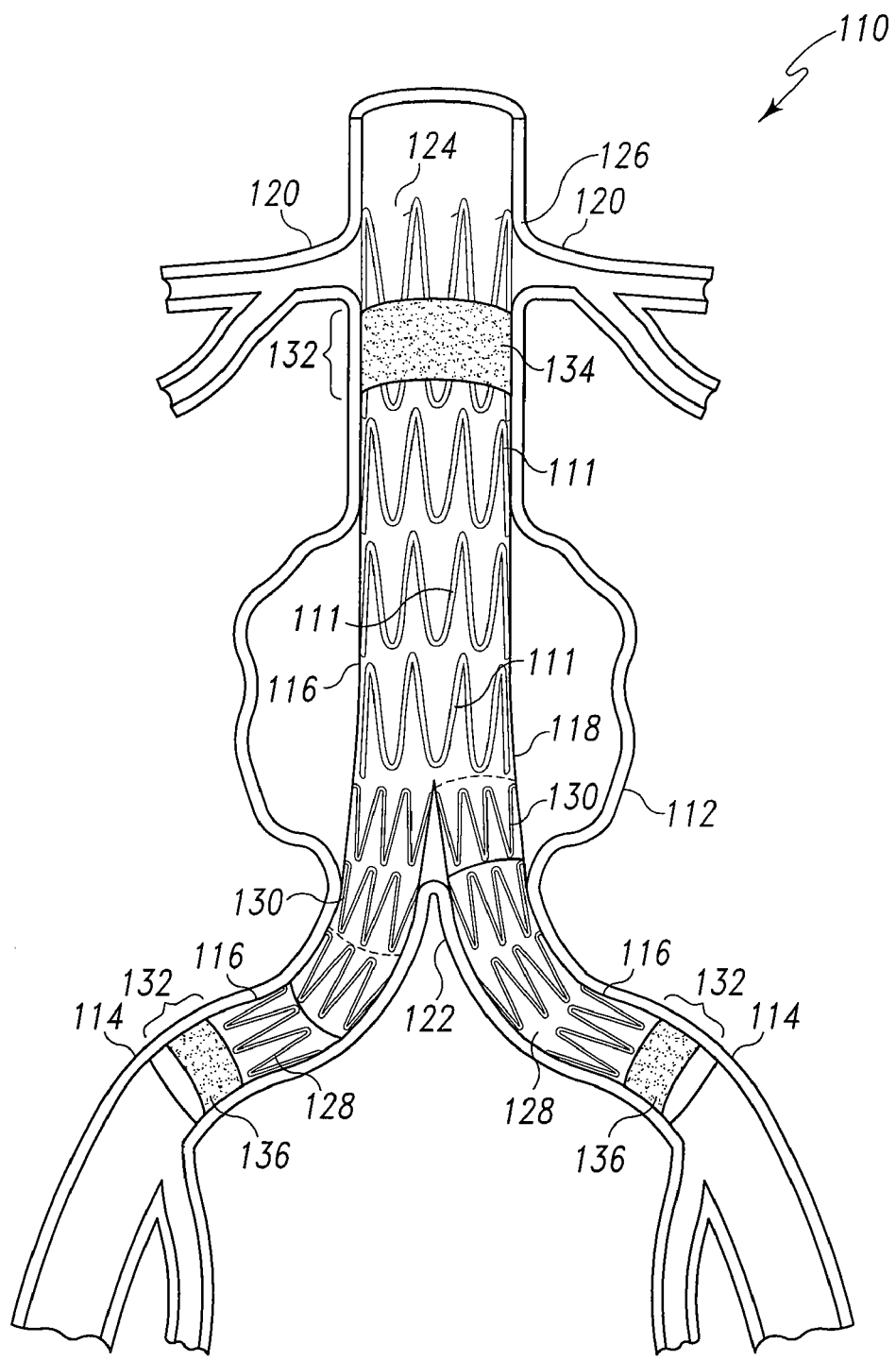
FIG. 15 depicts a modular bifurcated aortic stent graft with ECMM bands, implanted within an aneurysmal aorta.

FIG. 15 shows an example of a modular bifurcated stent graft 110 deployed within an aneurysmal aorta 112 and both iliac arteries 114. The ZENITH® stent graft described above is an example of such a modular, bifurcated stent graft. The prosthetic modules 116 that make up the stent graft 110 are generally tubular, so that fluid can flow through the stent graft 110, and are preferably made of polyester, PTFE or other suitable materials, such as those listed above. The main body 118 extends from the renal arteries 120 to near the bifurcation 122. Multiple zig-zag stents 111 are sutured along the length of the stent graft 110. A suprarenal fixation stent 124 anchors the main body 118 to the healthier, preferably non-aneurysmal tissue 126 near the renal arteries. Two iliac extension modules 128 extend from the iliac limbs 130.

The stent graft 10 will preferably achieve a blood-tight seal at the sealing zones 132 on both ends of the aneurysm 112, so that the aneurysm 112 will be excluded. In the particular embodiment shown in FIG. 15, the stent graft 110 contacts the vascular tissue below the renal arteries 120, around the bifurcation 122 and at the iliac limbs 130 and extensions 128. In this embodiment, a seal is preferably achieved at or near the renal arteries 120 and at the end of the iliac limbs 130. This will help exclude the entire aneurysmal region and, as a result, the hemodynamic pressures within the aneurysm 112 may be reduced. These seals may be improved by the incorporation of ECMM at the external sealing zones 132. FIG. 15 shows ECMM incorporated in bands 134, 136 above and below the aneurysm 112. The ECMM bands may, for example, be place within 3 cm or one or more ends of the prosthesis. ECMM can be incorporated into these locations in a variety of different ways, as described below.

Figure 16:
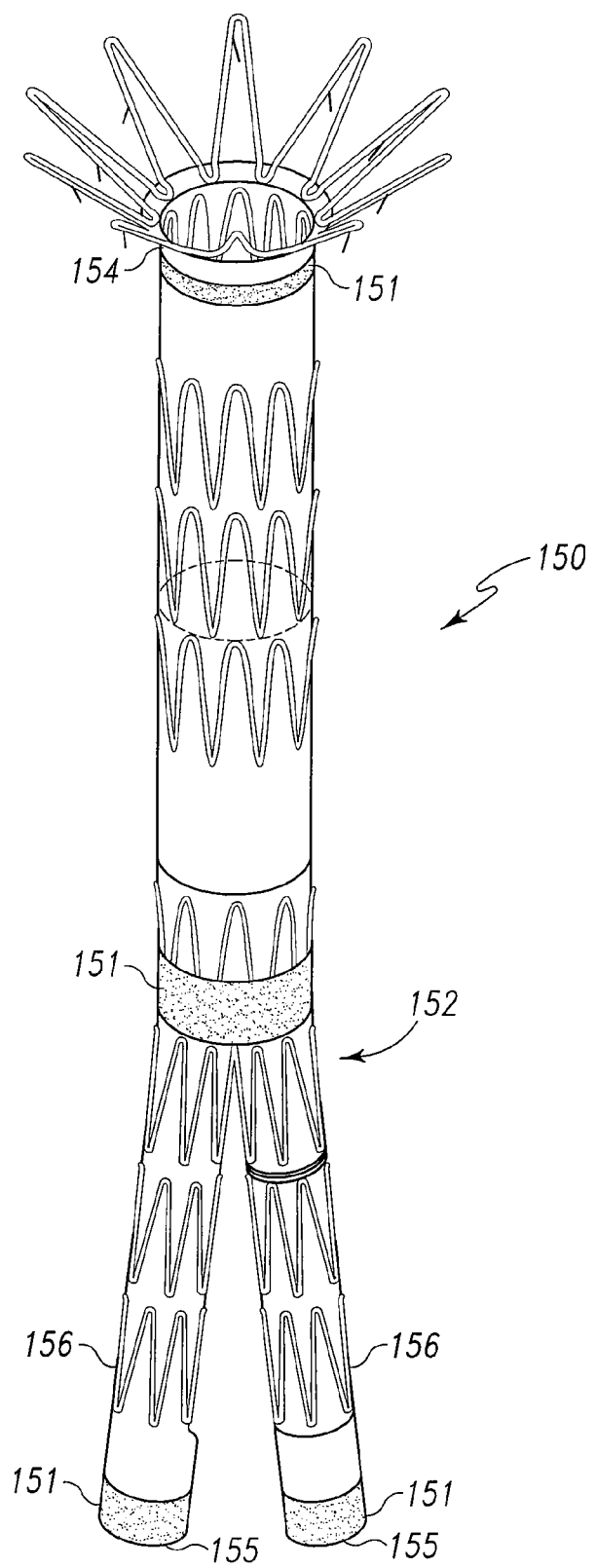
FIG. 16 depicts a modular bifurcated aortic stent graft with ECMM bands.
Figure 17:
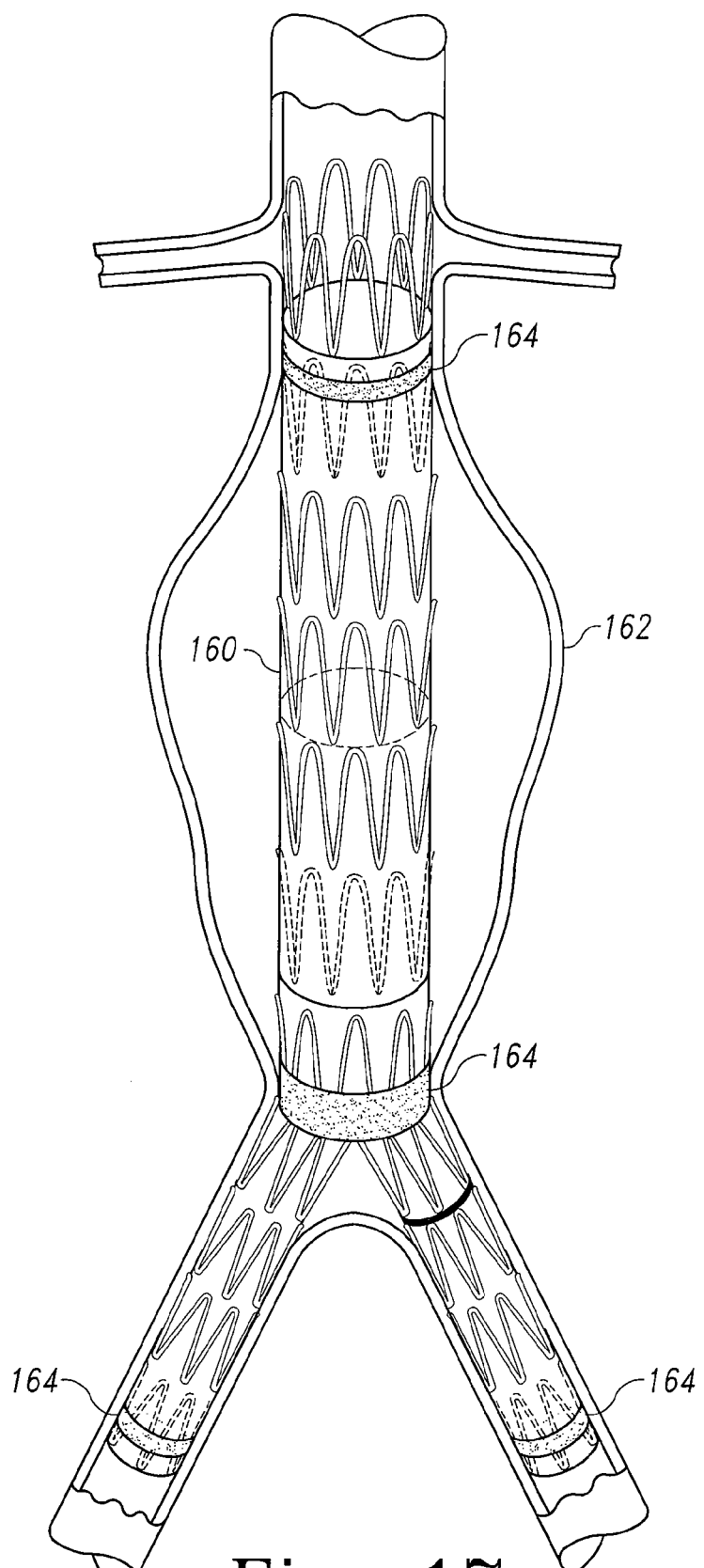
FIG. 17 depicts the stent graft similar to that of FIG. 16 after implantation within an aneurysmal aorta.

FIG. 16 shows a three-piece modular bifurcated stent graft 150 designed for deployment into an aorta. In this embodiment, ECMM 151 is incorporated near the bifurcation 152, as well as near the proximal opening 154 of the stent graft 150 and at the ends 155 of the iliac limbs 156. FIG. 17 shows a stent graft embodiment 160 similar to that of FIG. 16 after implantation. In FIG. 17, ECMM bands 164 contact the surrounding vessel wall 162 at or near the external sealing zones.

Figure 18:
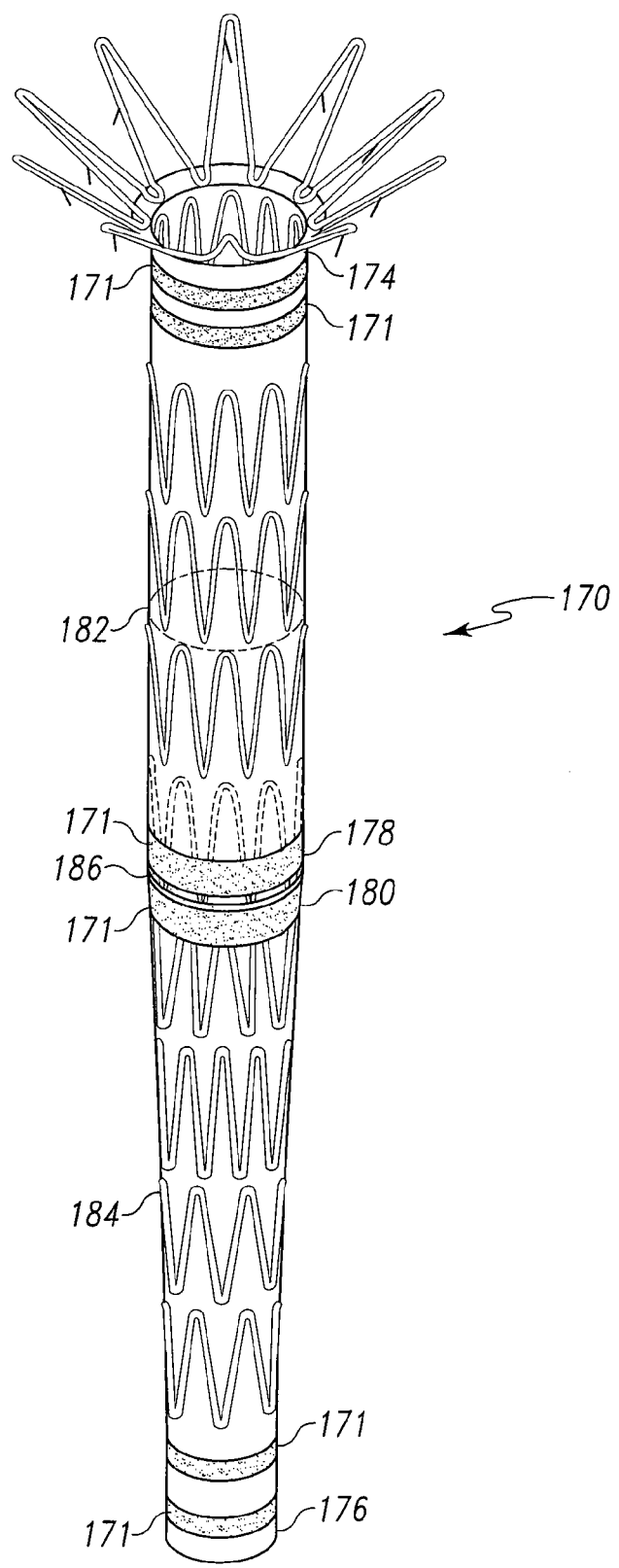
FIG. 18 depicts an aortouni-iliac stent graft with ECMM bands adjacent its openings and near its modular interconnection.

FIG. 18 shows a modular aorto-uniiliac stent graft 170 similar to that described in U.S. patent application Ser. No. 10/104,672, filed Mar. 22, 2002, which is incorporated herein by reference. ECMM 171 is incorporated in dual bands at both ends 174, 176 and in single bands 178, 180 on each of the two modules 182, 184 at or near the overlap region 186. The bands 178, 180 at the overlap region 186 are preferably placed so that following deployment of the modules 182, 184, the ECMM bands are nearly contiguous or overlapping. Multiple bands such as those employed on either end 174, 176 of the stent graft 170 can be used in the place of single bands on any type of endoluminal prosthesis. The use of ECMM 171 at or near the overlap region 186 can improve the seal between the modules 182, 184 and prevent migration of the graft 170.

Figure 19A:
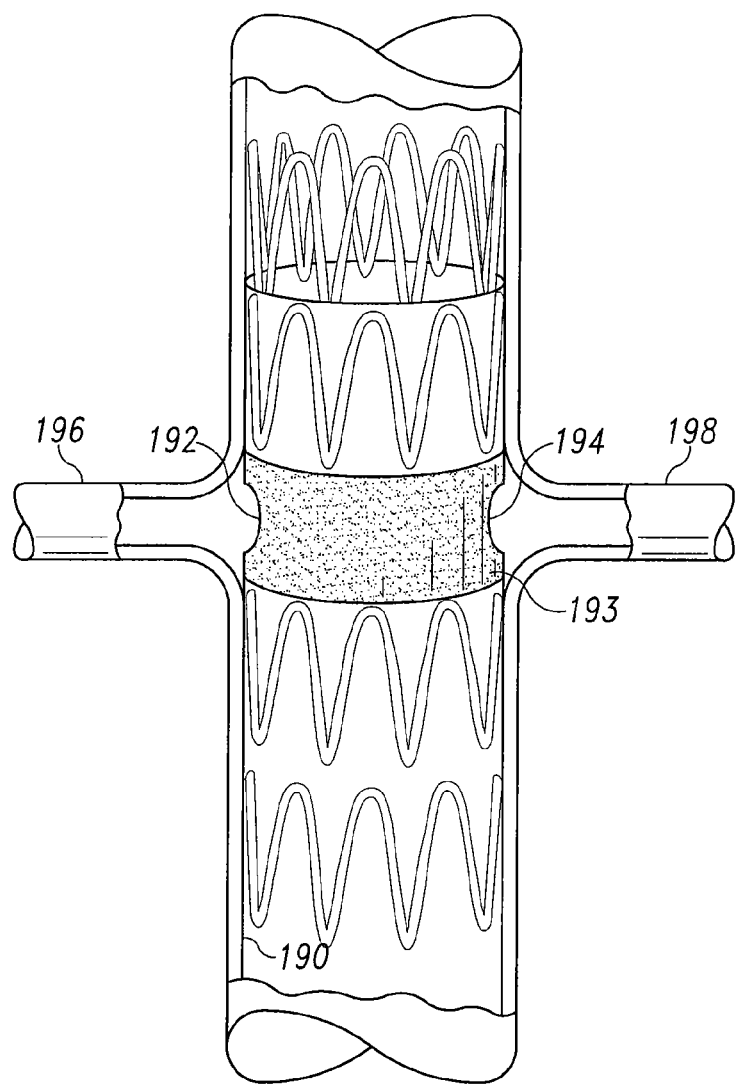
FIG. 19a depicts an implanted fenestrated aortic stent graft, with an ECMM band encompassing the fenestrations.
Figure 19B:
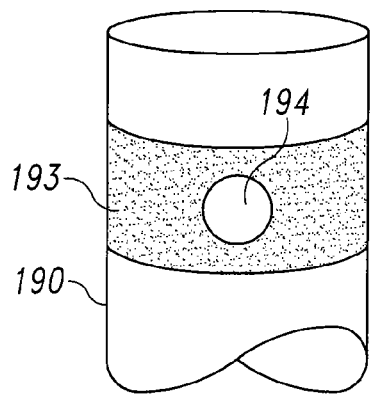
FIG. 19b depicts a partial side view of the stent graft of FIG. 19a before implantation.
Figure 19C:
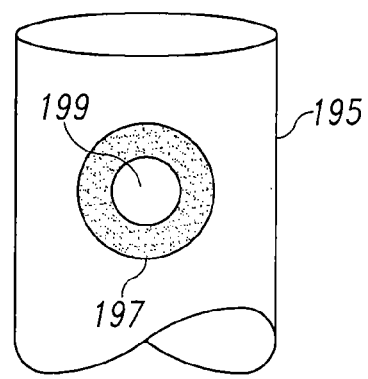
FIG. 19c depicts a fenestrated stent graft with an ECMM band around the fenestration.
Figure 20A:
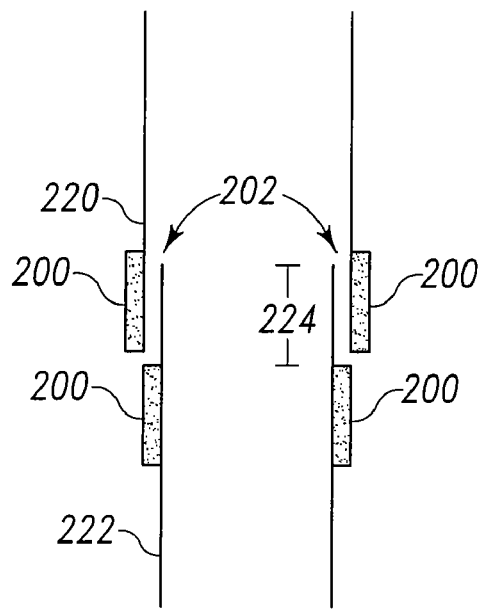
Figure 20B:
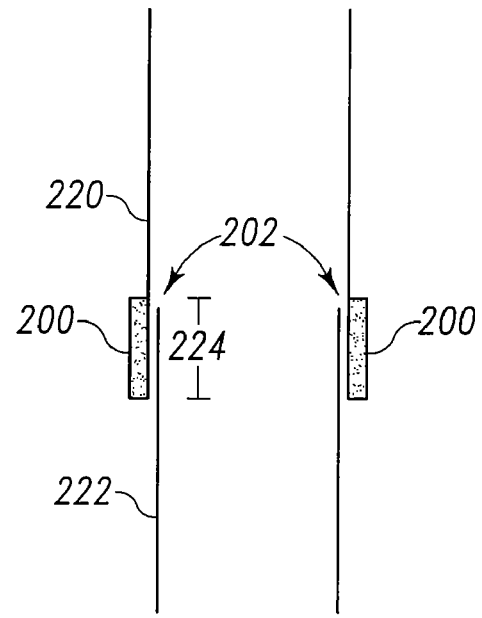
Figure 20C:
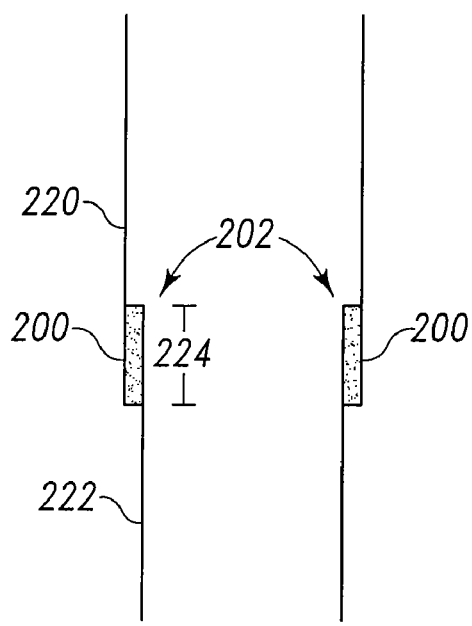
Figure 20D:
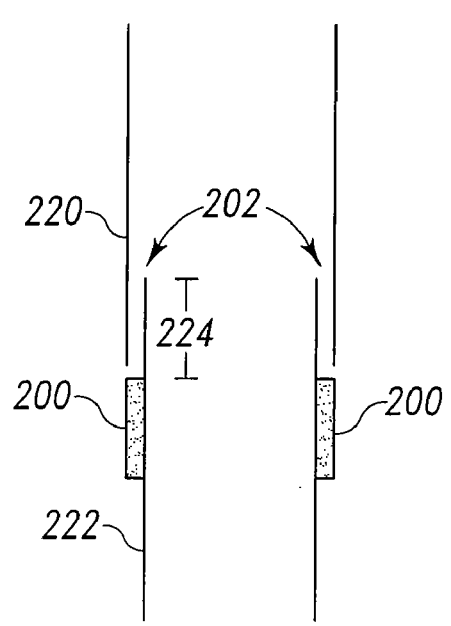

As shown in FIG. 19, ECMM 193 can be incorporated into a fenestrated prosthetic module 190 similar to that described in U.S. Pat. No. 6,524,335, which is incorporated herein by reference. FIG. 19*a* shows an aortic stent graft with fenestrations 192, 194 for each renal artery 196, 198. ECMM 193 is preferably incorporated around the fenestrations 192, 194 to assist sealing. Stents or branch vessel stent grafts (not shown) can be deployed through the fenestrations 192, 194. FIG. 19*b* shows a side view of the embodiment of FIG. 19*a*. FIG. 19*c* shows a fenestrated stent graft 195 that has an ECMM band 197 incorporated around the individual fenestration 199.

FIG. 20 shows seven of the possible positions for ECMM 200 relative to an overlap 202 between the two prosthetic modules 220, 222. ECMM 200 is preferably incorporated on both the outer modules 220 and the inner module 222 as shown in FIGS. 20*a* and 20*e*-*g* although the material may be incorporated on only one of the modules, as shown in FIGS. 20*b*-*d*. In FIG. 20*c*, ECMM is incorporated in the overlap 202 between the two modules 220, 222. A portion of the outer module 220 near the ECMM 200 can be perforated or otherwise porous as described in greater detail with reference to FIG. 21. These locations for the ECMM 200 include: the outer surface of the outer graft near the terminus at the overlap, the outer surface of the inner graft adjacent to the overlap and the overlap region. ECMM 200 may be incorporated into any, some or all of these locations to improve sealing and/or inhibit migration.

Figure 21:
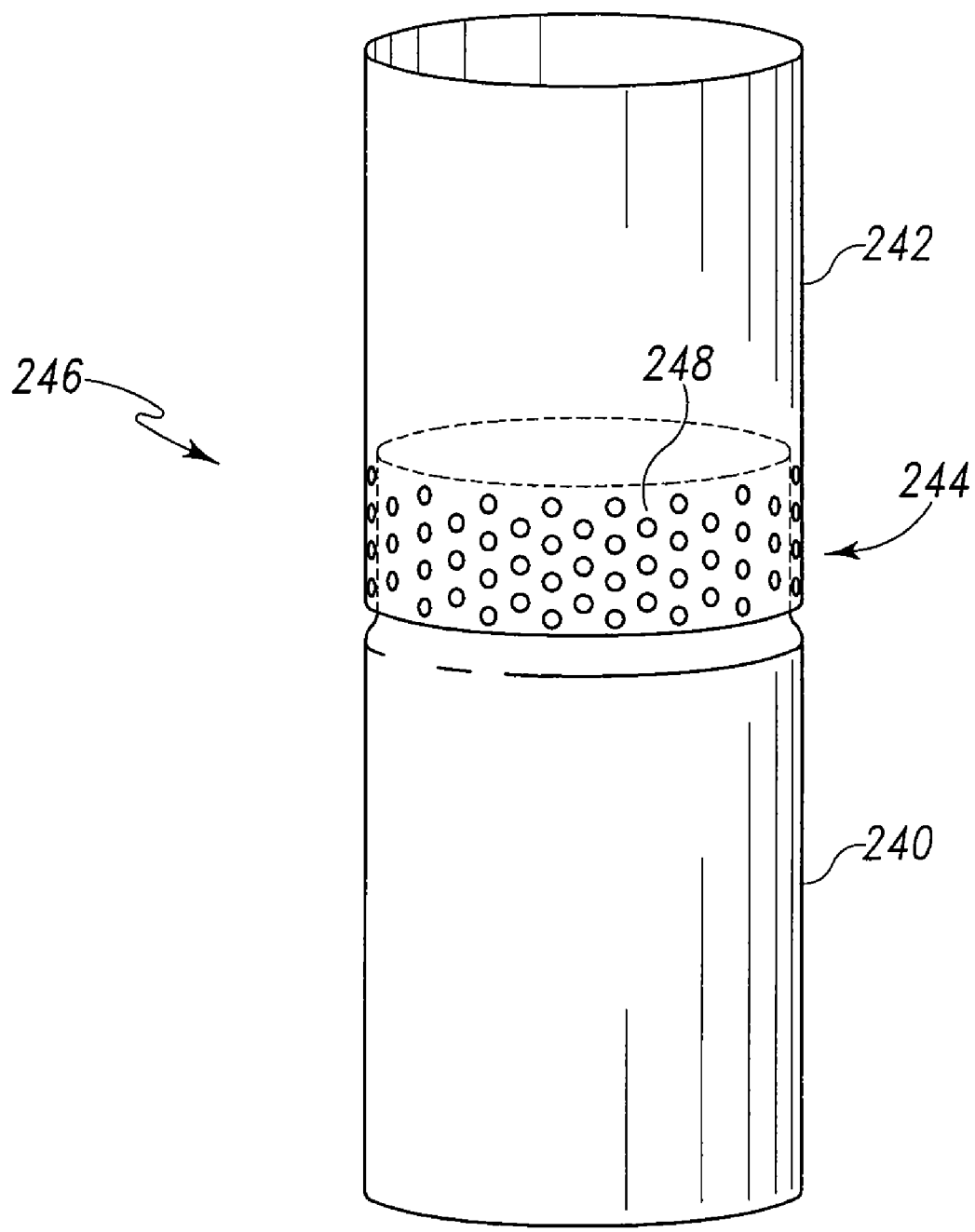
FIG. 21 depicts the interconnection of two prosthetic modules where ECMM is incorporated into the inner prosthetic module and exposed through the pores in the outer prosthetic module.

FIG. 21 shows an interconnection between two prosthetic modules 240, 242. In this particular embodiment, ECMM is incorporated into the inner prosthetic module 240 in the arrangement of FIG. 20*c*, but is exposed to the exterior surface 244 of the graft 246 through porosity 248 in the outer prosthetic module 242. In the embodiment shown, the porosity is woven into the outer prosthetic module 242, although the porosity 248 can also be the result of the pores between the fabric's warp and weft, or be otherwise formed into the fabric by any means known to those of skill in the art. This arrangement allows the cellular infiltration and other processes described above to occur, thereby causing the surrounding vascular tissue to meld with the inner prosthetic module, while simultaneously fixing the outer and inner prosthetic modules 240, 242 in place.

Figure 22:
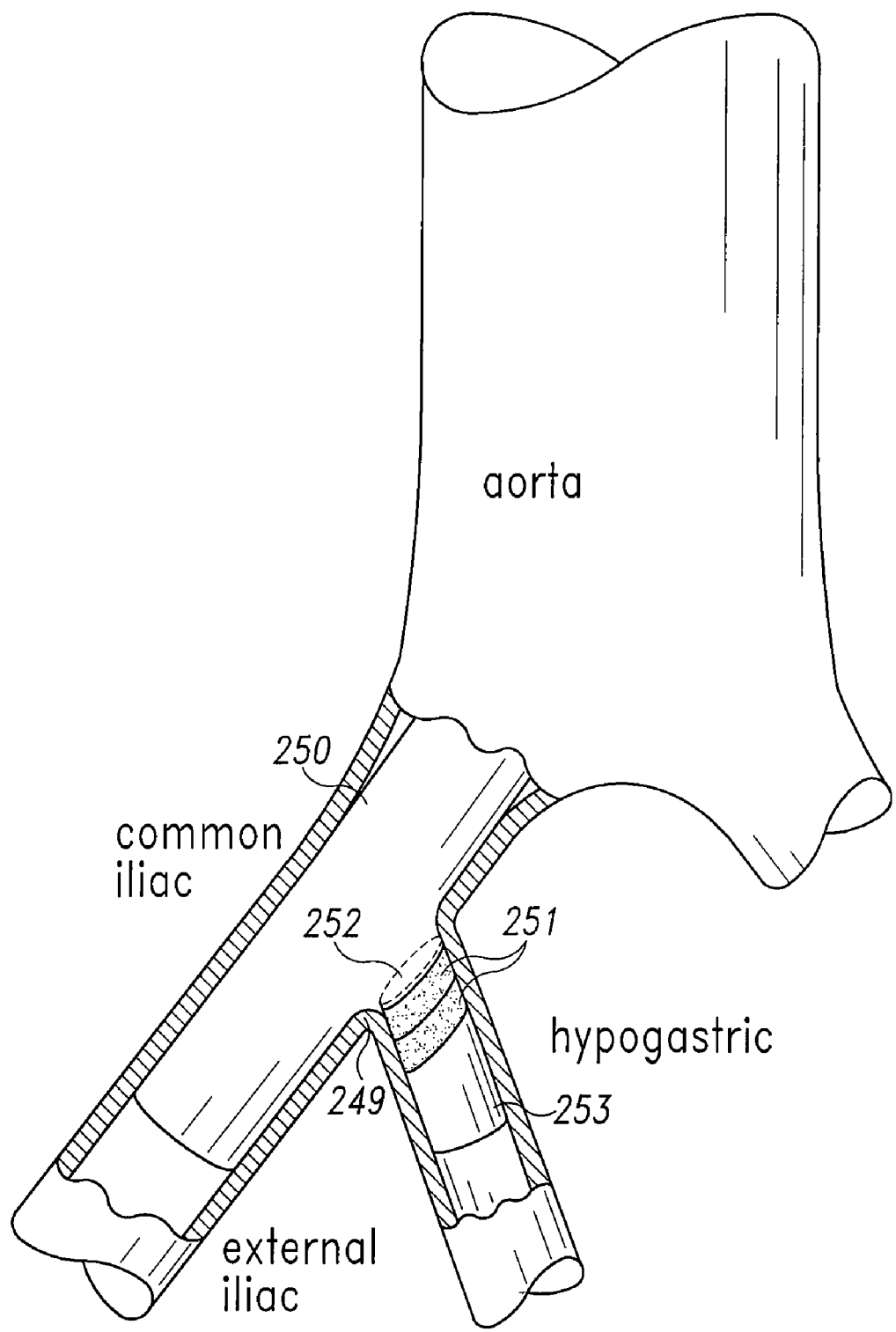
FIG. 22 depicts an iliac limb prosthetic module interconnected with a hypogastric branch module and ECMM bands near the interconnection.

In FIG. 22, a portion of a branched prosthesis 250 is shown. ECMM 251 can be incorporated at or near the site of interconnection between the branch limb 252 and the branch extension 253. ECMM 251 can also be incorporated at other external sealing zones, such as near the bifurcation 249.

The method of incorporation of ECMM generally varies depending on its form. ECMM filaments or thread can be incorporated into a prosthesis by, for example, weaving, knitting or sewing. Fluidized or powdered forms of ECMM can also be incorporated into a prosthesis. These methods of incorporation can be described as "integration," i.e. making the ECMM a part of the prosthesis or graft material layer. If, however, the ECMM is in pieces or strips, it may, for example, be incorporated into the prosthesis by affixing the ECMM to the graft with sutures, staples or the like, wherein the ECMM is in a separate layer adjacent the graft or prosthesis material.

Figure 23A:
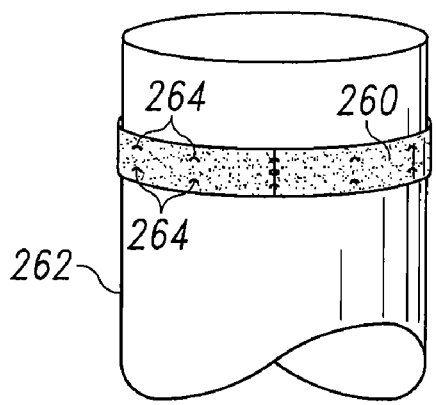
FIG. 23a depicts a band of ECMM sutured around a tubular graft.

In one embodiment, ribbons, strips, bands or other sections of ECMM are affixed to the graft by any method known to those of skill in the art. Before ECMM is attached to the endoluminal graft, it is preferably cut into a strip or filament of appropriate shape or length. As shown in FIG. 23*a*, a substantially rectangular strip of ECMM 260 that is approximately the circumference of the stent graft 262 may be sutured to graft at multiple locations to form a single-layer band around the stent. Sutures 264 connecting ECMM to the graft 262 are preferably tied periodically through the band to help keep it in place. ECMM can be affixed using sutures 264, stitching, glue, staples or any other method known to those of skill in the art.

These sections of ECMM are preferably disposed on the graft material so that ECMM is in between the stent and the graft material. This may help facilitate the incorporation of the stent into the surrounding tissues once the graft is implanted. Coating the stent itself with ECMM may further assist this process. Alternatively, the ECMM strip may be sandwiched between the stent and the graft material.

Figure 23B:
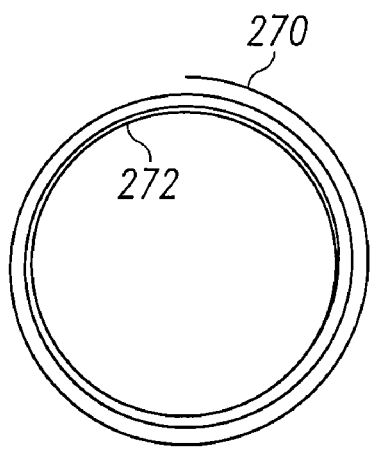
FIG. 23b is a schematic view of a multi laminate ECMM construct affixed to a tubular graft.
Figure 23C:
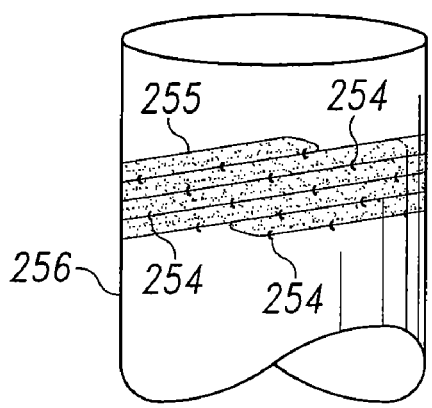
FIG. 23c depicts a helical band of ECMM sutured around a tubular graft.

A strip of ECMM 270 can be wrapped repeatedly around the graft 272 to create a multi-laminate, thicker ECMM construct, as shown in FIG. 23*b*, or can be wrapped helically as shown in FIG. 23*c* to create a wider ECMM construct 255. Preferably, the strip of ECMM is sutured to the fabric of the prosthesis 256, as shown in FIGS. 23*a*-*c*. Alternatively, a multi-laminate band may first be formed, and then affixed to the prosthesis material. An ECMM gel, preferably made from SIS, can then be used as a "binder" to fill the pores created by the stitching process. Any fibers protruding from the fabric can form a mechanical scaffolding to hold the SIS gel in place.

Figure 23D:
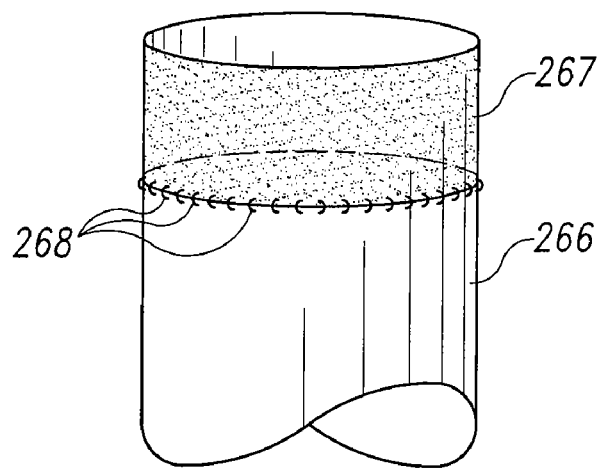
FIG. 23d depicts a tubular ECMM construct that forms the end of a tubular graft.
Figure 23E:
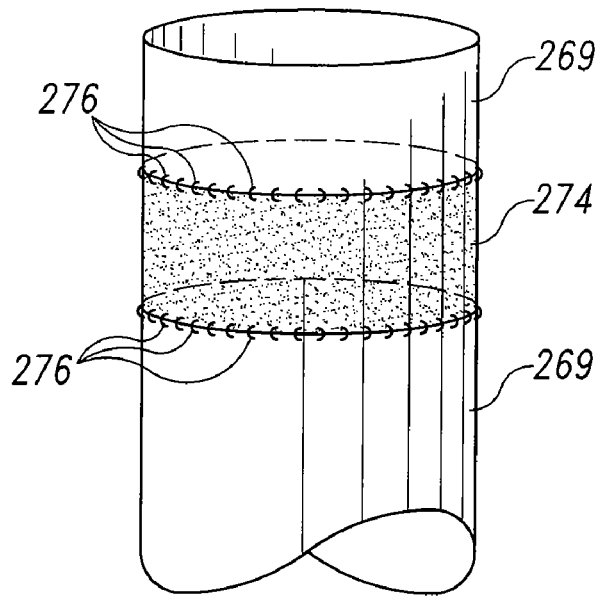
FIG. 23e depicts an intervening ECMM band that connects two discontinuous synthetic tubes.

As shown in FIG. 23d, a tubular ECMM construct 267 can be used to extend the length of the synthetic tube 266. The tubular ECMM construct 267 can be attached with sutures 268, or by any means known to those of skill in the art. Similarly, as shown in FIG. 23e, a tubular ECMM construct 274 can connect two discontinuous synthetic tubes 269 using sutures 276, or other means known to those of skill in the art.

An ECMM sheet, preferably made from SIS, may be vacuum pressed onto the synthetic graft material with the use of an ECMM gel as an adhesive. The use of ECMM gel, preferably made from SIS, as a "glue" both connects the ECMM sheet to the graft as well as promoting further tissue ingrowth. One possible manufacturing process is to apply an SIS gel and SIS sheet on to the outside of the graft and then "vacuum pull" the graft so that SIS gel can penetrate the graft, subsequently polymerize the composite graft in the oven at 37° C. for 20 minutes and then freeze dry and for vacuum press the composite graft.

Furthermore, an SIS sheet can be stitched on to a synthetic graft so as to form a secure and permanent mechanical attachment. SIS gel can then be used as a "binder" by following the steps described in the second method to fill the pores created by the stitching process and further, any protruding fibers can form a mechanical scaffolding to hold the SIS gel in place. The stitching can be done using a biocompatible thread such as a suture thread or by the use of a wire thread.

In one embodiment, multiple layers of purified submucosa in the overlapped region are affixed to one another or to the prosthesis by treatment with a cross-linking agent. An aldehyde, such as formaldehyde, or more preferably glutaraldehyde, may be used as a cross-linking agent or adhesive. In one embodiment the seam of the wrapped tube of purified submucosa can be "spot welded" using glutaraldehyde to ensure that the end piece does not come loose. In accordance with this embodiment, a cotton swab moistened with a glutaraldehyde solution (or other cross-linking or adhesive agent) is applied along the overlapped region forming the seam. The glutaraldehyde concentration is preferably about 0.1 to about 1.0%, more preferably about 0.5%. In one embodiment the entire graft construct can be immersed into a solution of glutaraldehyde to fix the multiple layers of the tube of purified submucosa to one another. In addition, the multiple layers of purified submucosa in the overlapped region can be sutured to one another, and in one embodiment the layers of the overlapped region are fixed with sutures in the absence of treatment with a cross-linking agent. As an alternative to aldehydes, methylcyanoacrylate or similar glues can be used to weld layers or pieces of ECMM to each other or to the prosthesis material.

Figure 24:
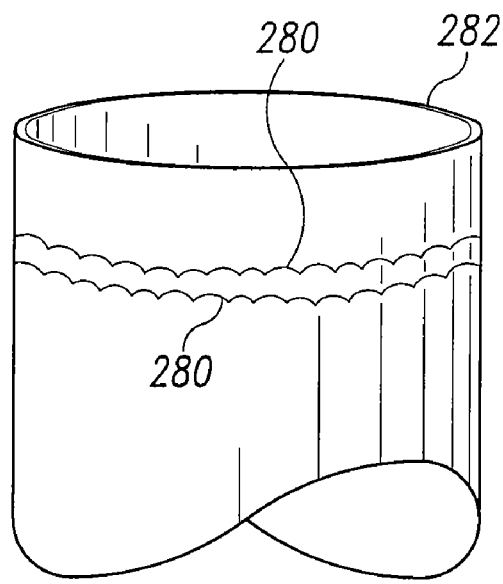
FIG. 24 depicts two ECMM filaments or thread sewn into a stent graft.
Figure 25:
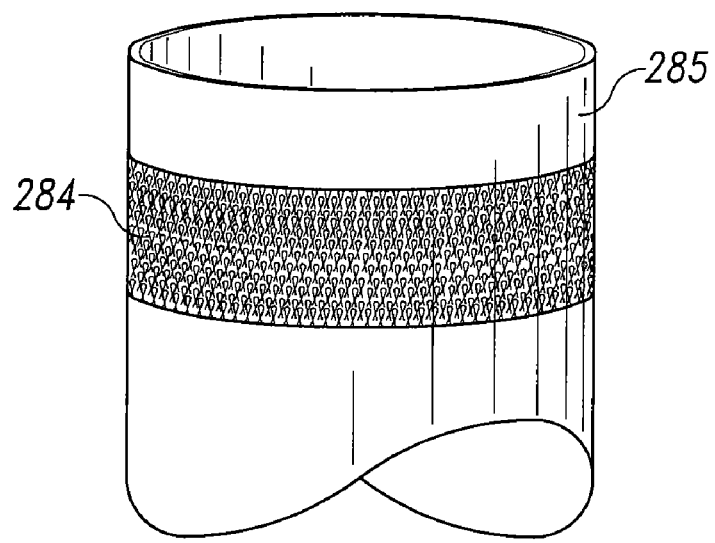
FIG. 25 depicts ECMM filaments or thread that form a terry cloth surface on the stent graft.
Figure 26:
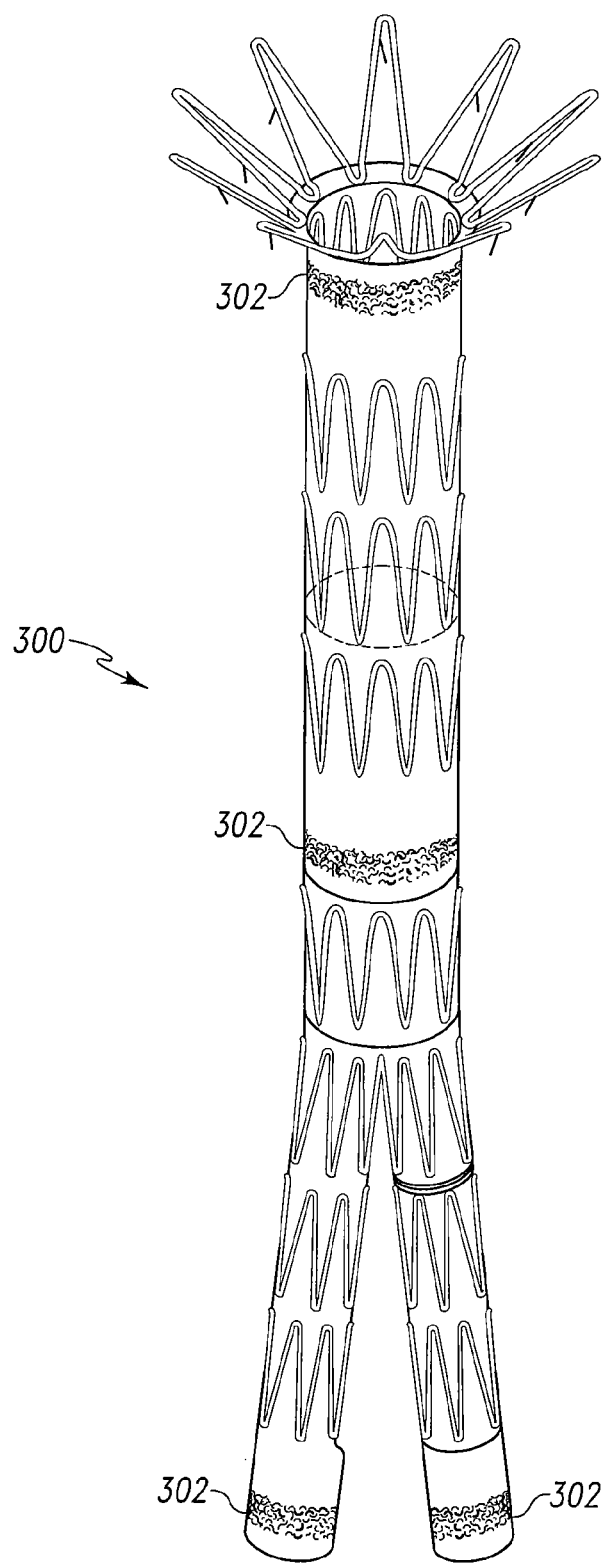
FIG. 26 depicts a bifurcated aortic stent graft that has terry cloth ECMM at the modular termini and near the bifurcation.

As an alternative to affixing strips or pieces of ECMM, ECMM can be incorporated into a prosthesis material such as polyester or PTFE. This can be accomplished in any way known to those of skill in the art. As shown in FIG. 24, ECMM filaments or threads 280 can be sewn into the graft 282. The thread employed in this method can be manufactured from a combination of ECMM and synthetic filaments; it can also be manufactured from synthetic filaments that are impregnated with fluidized or powdered ECMM, as described above. Filaments or threads 280 can be sewn so that they are substantially flush with the outer surface of the graft 282. As shown in FIG. 25, ECMM can be sewn into the prosthesis material so that loops 284 extend beyond the surface of graft material 285 to form a terry cloth or velour surface. A stent graft 300 with terry cloth ECMM bands 302 is shown in FIG. 26.

Figure 27A:
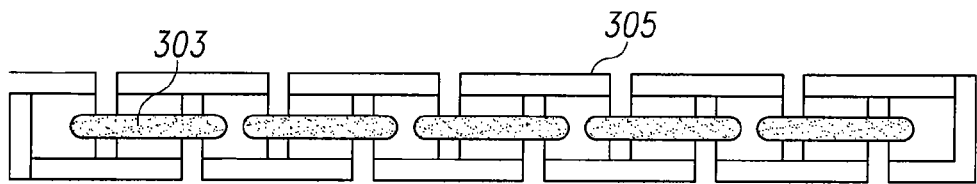
FIGS. 27a-d depict various stitches that can be used to sew ECMM filaments or thread into the stent graft.
Figure 27B:
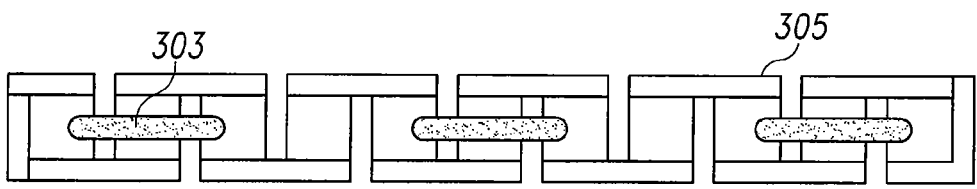
Figure 27C:
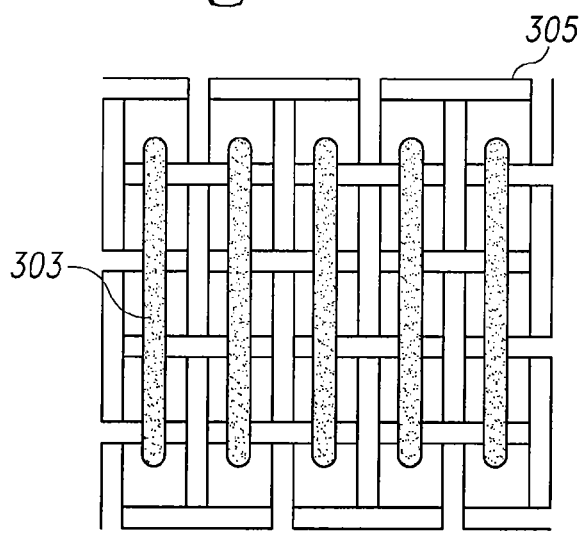
Figure 27D:
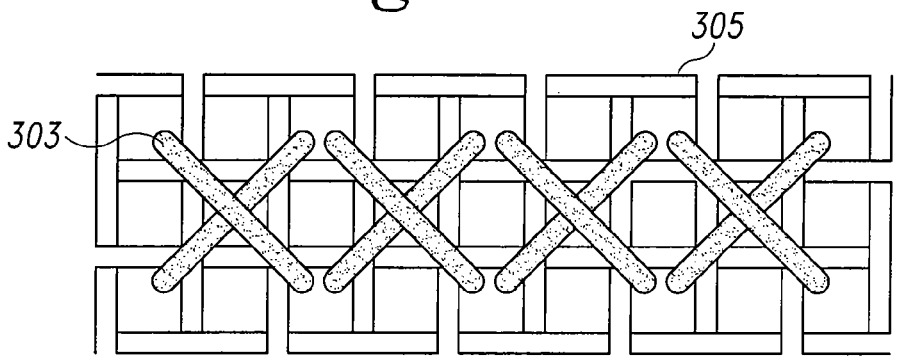

Any stitch known to those of skill in the art may be utilized to incorporate ECMM 303 with the prosthesis material 305, including straight stitches, such as the double running stitch (FIG. 27a) or single running stitch (FIG. 27b); dense filling stitches such as the satin stitch (FIG. 27c); or cross stitches (FIG. 27d). More than one stitch may be used in a given ECMM band. ECMM is preferably incorporated in the external sealing zones described above. ECMM filaments can be spun or woven into thread prior to incorporation into the graft fabric; such thread can also include synthetic materials.

Figure 28A:
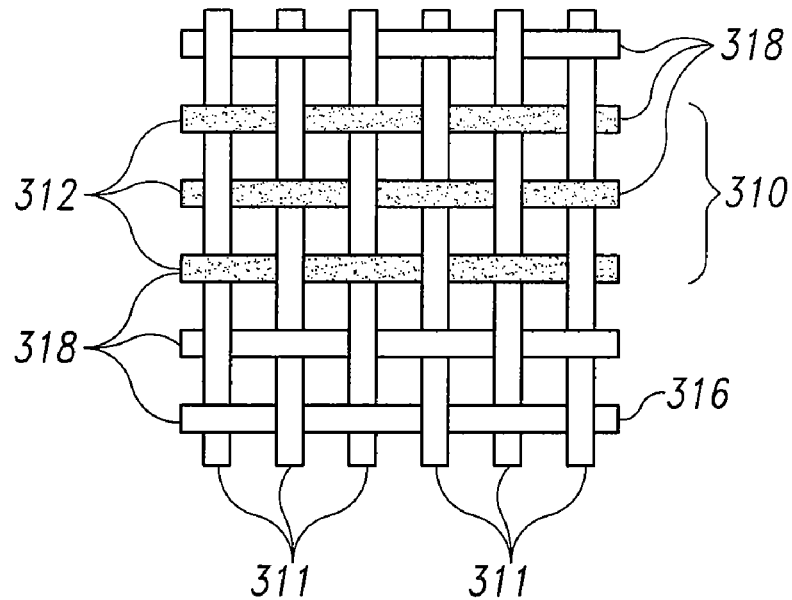
FIGS. 28a-b depict ECMM filaments or threads woven into the graft fabric.
Figure 28B:
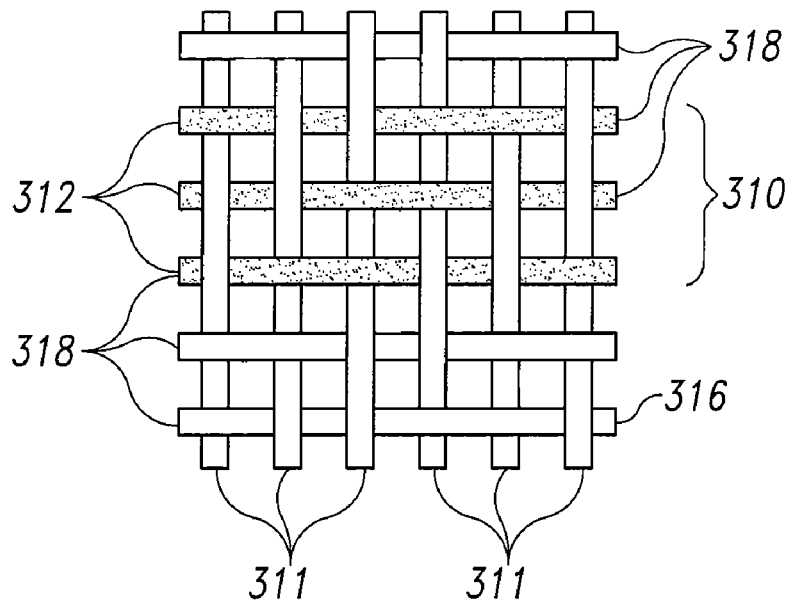

Alternatively, ECMM filaments or thread can be selectively integrated into a graft fabric as that material is woven. For example, one or more stripes 310 of ECMM filaments or thread 312 can be woven into a plain (FIG. 28a) or twill weave (FIG. 28b) polyester fabric 316. In both FIGS. 28a and 28b, the ECMM filaments or thread 312 are incorporated only into the weft 318, not the warp 311. For some fabrics, it may be preferable to incorporate ECMM into the warp 311. A terry cloth ECMM band can also be created when the prosthesis material is being woven using methods known to those of skill in the art.

The powder or fluidized form of ECMM as described above may also be integrated into the synthetic material of the prosthesis in a variety of ways. For example, the fluidized EMCC may be applied to a banded region near the terminus and allowed to dry. A band on the prosthesis material may be impregnated with the powdered form of ECMM, or may be stitched with thread or filaments that contain a powdered form of ECMM. The term "impregnation" means providing for the presence of one or more components inside the graft material, in particular in the interstices of the synthetic material. The term "interstices" means spaces that intervene between parts of the graft material. Interstices include pores, cavities, and spaces. For example, interstices are between fibers of the textile material. Additionally, the stents themselves, or portions thereof, may be coated with a fluidized or powdered form of ECMM. Alternatively, ECMM could be adhered to the stents using a separate adhesive.

In particular, an ECMM gel, preferably made from SIS, may be used to impregnate a relatively porous graft. The natural porosity of a woven fabric (which can be altered by various weaving or post-weaving techniques) can facilitate infusion into the graft of a SIS gel by applying a vacuum on one side of the graft and "pulling" the SIS gel into the interstices which form the natural porosity of the graft.

ECMM coating is preferably avoided on portions of uncovered stents designed to traverse branch vessel ostia, such as the renal ostia. Furthermore, the coating may be selectively disposed only on the uncovered anchoring stents, or portions thereof. Portions of the stent that are particularly suited for ECMM are those that are prone to contact the surrounding tissue. In order to control whether or not the stents themselves are coated by a fluidized or powdered ECMM, the stents may be attached before or after the ECMM treatment. If, for example, the stent is already sutured to the graft material at the time the graft material is impregnated with fluidized ECMM, it is likely that the stent will take on its own layer of ECMM. If the stent, particularly an uncovered stent, is supposed to transverse the ostium of a branch vessel, it may be preferable for the fluidized or powdered ECMM to be removed from parts of the stent so that the blockage of the ostia does not develop. In other stent grafts, it may be beneficial to ensure that sections of the stents are covered with fluidized or powdered ECMM.

Figure 29:
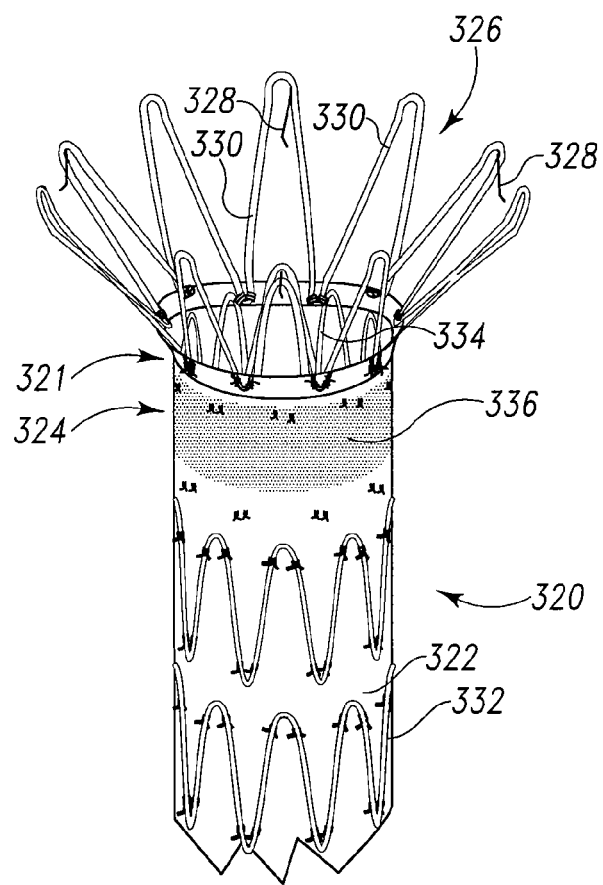
FIG. 29 depicts a perspective view of a portion of a stent graft having an ECMM band.

FIG. 29 shows a perspective view of a portion of a stent graft 320 incorporating an ECMM band 336. The stent graft 320 has a tubular body 322 of a biocompatible material such as the woven polyester described above. Along the length of the stent graft 320 there are self-expanding Z-stents 332 stitched to outside of the tubular body 321. At the proximal end 324 there is an internal self expanding Z-stent 334 stitched to the body 321. When the stent graft 320 is deployed into a vessel of a human or animal body such as an aorta, this proximal Z-stent 334 provides pressure against the wall of the aorta in the landing zone. By having the Z-stent 334 within the tubular body 322, a smoother outer surface is presented to the wall of the aorta to provide a degree of sealing.

There is also a proximally extending uncovered self-expanding Z-stent 326. This proximally extending Z-stent 326 has barbs 328 extending from struts 330 of the stent 326. When the stent graft 320 is deployed into a vessel of a human or animal body such as an aorta the barbs 328 engage into the wall of the aorta, and provide a purely mechanical immediate fixation of the stent graft into the vessel. Pulsatile forces may cause migration, in turn causing the barbs to tear the wall of the aorta.

Figures 30, 31:
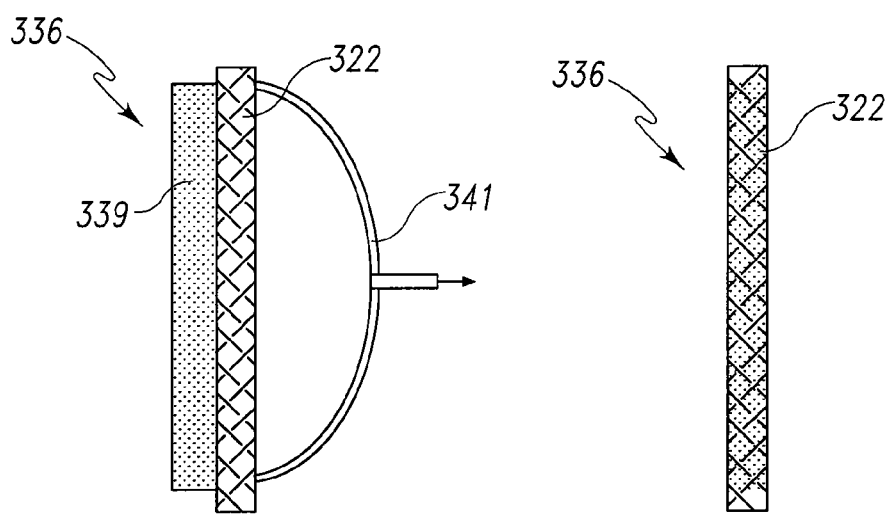
FIG. 30 depicts an enlarged view of a portion of a graft material showing how ECMM can be impregnated into the graft material.
FIG. 31 depicts an enlarged view of a portion of the resulting graft material.

In the portion of the stent graft 320 just distal of the proximal end 324 there is a band 336 around the circumference of the stent graft 320 which incorporates an ECMM, preferably an SIS gel or a digest of SIS impregnated into the graft material tube 322. FIGS. 30 and 31 show this process in detail.

FIG. 30 shows a gel or digest of SIS 339 being applied to one surface of the graft material 322 in the band 336 and then a vacuum being applied by means of a vacuum hood 341. The SIS gel or digest 339 is thereby drawn into the graft material 322 to give the result shown in FIG. 31. The natural porosity of the graft material can be altered by various weaving techniques to improve the amount of infusing into the graft of the SIS or by providing additional porosity in selected regions of the stent graft by drilling or ablating holes in the graft material using a laser or similar device. Such porosity may provide openings in the material of 20 to 100 microns.

The cell wall tissue can then grow into the graft material via the scaffolding provided by the SIS. Fixation occurs as the synthetic fiber/fiber bundles are surrounded by new tissue growth, such as the collagen based adventitia which forms a bio-mechanical attachment mechanism (between the graft and artery wall). Sealing will also be a by-product of the tissue growth through the SIS-impregnated graft. In addition, it is likely that the endothelial cells will grow into the SIS on the inside of the graft wall forming a very smooth surface resulting in a non-thrombogenic graft property. Further, the resulting tissue ingrowth will be biological active "alive" resulting in natural resistance to infection, as opposed to a purely synthetic graft.

FIGS. 32 to 34 show a further embodiment of the invention to provide enhanced biological fixation. In this embodiment, a sheet of ECMM 350, preferably made from SIS, is laid over the graft material 322 in the region 336 with an intermediate layer 352 of a SIS gel or digest. A vacuum 353 is applied by means of a vacuum hood 354 and the gel or digest drawn into the graft material 322 to give the result shown in FIG. 33 where the sheet of SIS 350 is adhered to the graft material 322 using the SIS gel as an adhesive. The composite is then polymerized by heating in an oven at 30° for 20 minutes and the resultant product is freeze dried or vacuum pressed to provide a product as shown on FIG. 34.

An SIS sheet is capable of providing a collagen scaffolding enhanced with natural porcine growth factors and other proteins. This manufacturing technique utilizes the SIS sheet and attaches the sheet to the graft material in a secure fashion. The SIS gel is used as both a "glue" to connect the SIS sheet to the graft as well as promote further tissue ingrowth as with the embodiment discussed above. Hence one possible manufacturing process is as follows: (a) apply the SIS digest and SIS sheet on to the outside of the graft and "vacuum pull" the graft so that SIS gel can penetrate the graft; (b) polymerize the composite graft in the oven at 37° C. for 20 minutes; and (c) freeze dry and for vacuum press the composite graft.

Another embodiment of the invention is shown in FIG. 35. In this embodiment a SIS sheet is attached to a graft material by use of metal or synthetic biocompatible fiber or thread. SIS sheet can be stitched on to a synthetic graft so as to form a secure and permanent mechanical attachment. This technique can be enhanced by using a matrix of protruding stitches. As a further enhancement an SIS gel can then be used as a "binder" by following the steps described in the embodiment shown in FIGS. 32 to 34 to fill the pores created by the stitching process and further, the protruding fibers can form a mechanical scaffolding to hold the SIS gel in place. The resulting SIS stitched composite structure will encourage cell growth through the fiber loops employing all the benefits of attachment and fixation described above.

One such structure is schematically illustrated in FIG. 35. The graft material 322 has a sheet of SIS 360 attached to it by stitching using stitches 362 which extend through both the SIS 360 and graft material 322 to a back stitch 363. An intermediate layer 365 of a SIS gel or digest can provide both a "glue" to connect the SIS sheet to the graft as well as promote further tissue ingrowth as with the embodiments discussed above. The stitches can be formed from stainless steel wire, nitinol wire or other suitable biocompatible material, including conventional sutures. Where the loops of the stitches extend beyond the SIS they may assist with biological fixation by engaging the wall of a vessel into which they are deployed and encouraging tissue growth around the loops.

Figure 36:
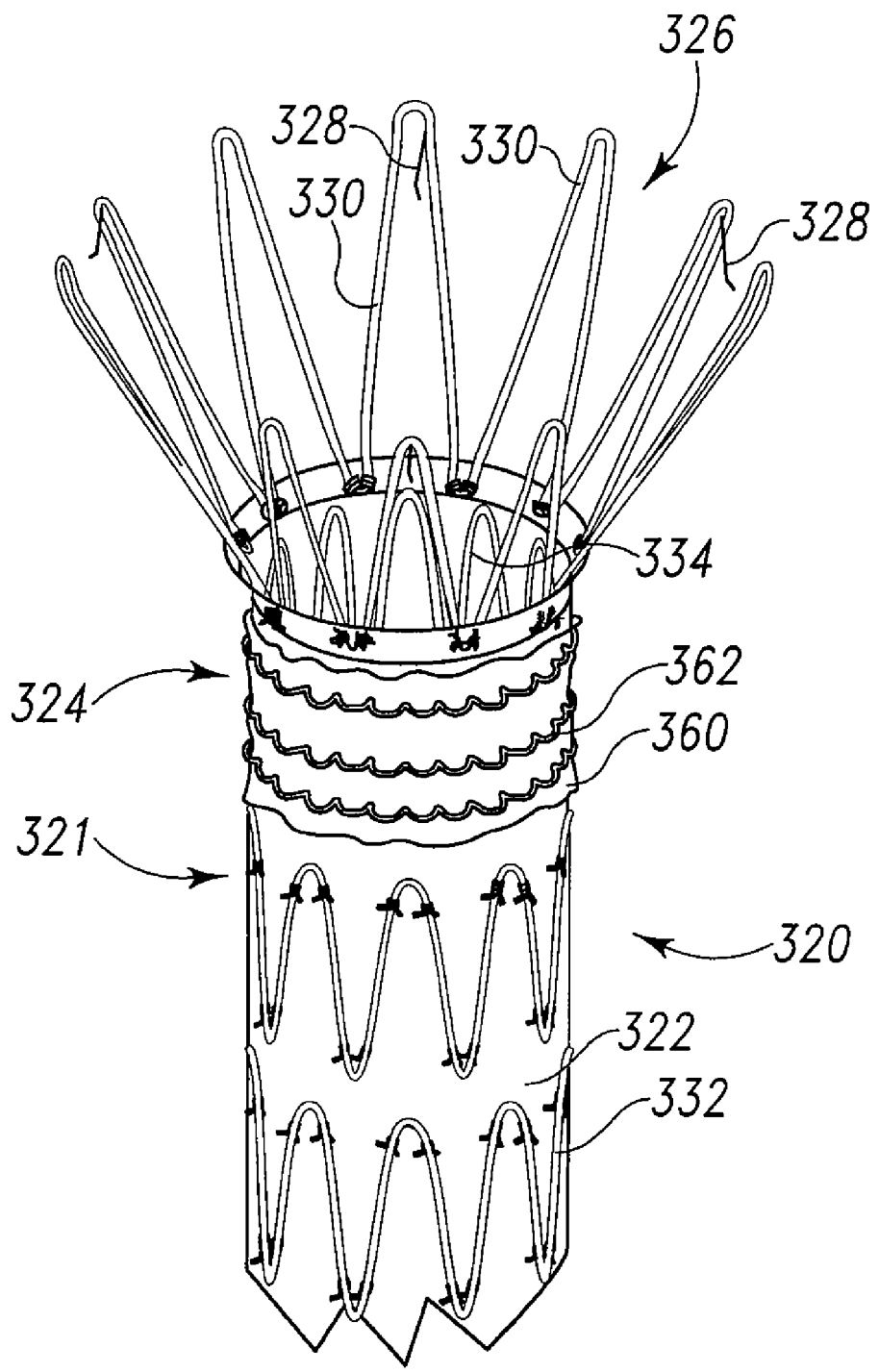
FIG. 36 depicts a perspective view of a portion of a stent graft incorporating the embodiment of the biological fixation arrangement shown in FIG. 36.
Figure 37:
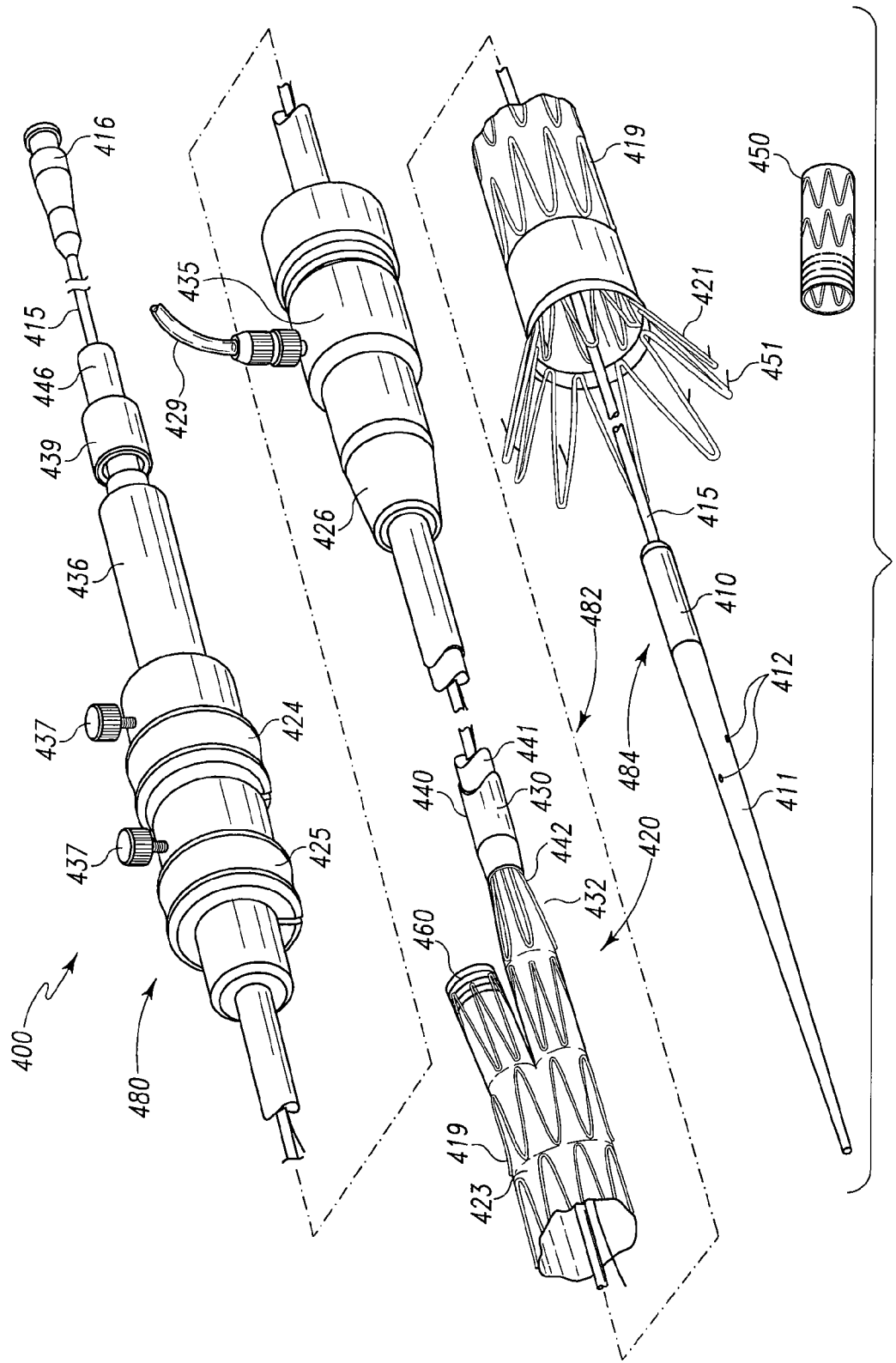
FIG. 37 depicts an introducer and a bifurcated stent graft.

FIG. 36 shows a perspective view of a portion of a stent graft incorporating the embodiment of the biological fixation arrangement shown in FIG. 35. In this illustration the same reference numerals are used as in FIG. 29 for the same components.

The stent graft 320 includes a sheet of SIS material stitched onto the proximal end region 324 of the stent graft 320 by means of wire stitches 362. The wire stitches 362 retain the SIS sheet material and have the added advantage that they provide apertures through the SIS and graft material which will permit cell growth through the material for enhanced biological fixation.

The wire stitches may also extend our from the surface of the SIS sheet and provide a matrix of radially outward protruding portions when the stent graft is deployed and a stent associated with the graft is providing radially outward pressure. These protruding portions may create a localized pressure (greater than 30 mmHg—to overcome capillary pressure) against the aorta wall initiating cell necrosis. After cell death the protruding portions will continue to impinge on the arterial wall leading to endothelial wall remodeling to accommodate the protruding portions. Each protruding portion may in time become completely encapsulated by tissue growth. In effect, the protruding portions introduced on the outside of the graft serve as scaffold for tissue (adventitia) to grow around each protruding portions creating a significant fixation and sealing mechanism.

The Introducer

FIG. 29 shows a ZENITH® self-expanding bifurcated stent graft 420 (like those available from Cook Incorporated, Bloomington, Ind. and sold under product code TFB1 through TFB5), and an endovascular deployment system 400, also known as an introducer 400, for deploying the prosthesis 420 in a lumen of a patient during a medical procedure. These items are each described in greater detail in PCT application WO98/53761. A self-expanding second prosthetic module 450 is also shown. Although not shown, ECMM can be disposed in bands in various locations on the stent graft of FIG. 29, as described further above.

The bifurcated prosthesis 420 has a generally inverted Y-shaped configuration. The prosthesis 420 includes a body 423, a shorter leg 460 and a longer leg 432. The bifurcated prosthesis 420 comprises a tubular graft material, such as polyester, with self-expanding stents 419 attached thereto. The self-expanding stents 419 cause the prosthesis 420 to expand following its release from the introducer 400. The prosthesis 420 also includes a self-expanding zig-zag stent 421 that extends from its proximal end. The self-expanding zig-zag stent 421 has distally extending barbs 451. When it is released from the introducer 400, the self-expanding zig-zag stent 421 anchors the barbs 451, and thus the proximal end of the prosthesis 420, to the lumen of the patient.

The self-expanding second prosthetic module 450 is configured to form a tromboning connection with the shorter leg 460 of the bifurcated prosthesis 420 and with an extension. A notch or scallop may be cut into the proximal end of the second prosthetic module 450 to facilitate deployment of the module.

The introducer 400 includes an external manipulation section 480, a distal attachment region 482 and a proximal attachment region 484. The distal attachment region 482 and the proximal attachment region 484 secure the distal and proximal ends of the prosthesis 420, respectively. During the medical procedure to deploy the prosthesis 420, the distal and proximal attachment regions 482 and 484 will travel through the lumen to a desired deployment site. The external manipulation section 480, which is acted upon by a user to manipulate the introducer, remains outside of the patient throughout the procedure.

The proximal attachment region 484 of the introducer 400 includes a cylindrical sleeve 410. The cylindrical sleeve 410 has a long tapered flexible extension 411 extending from its proximal end. The flexible extension 411 has an internal longitudinal aperture (not shown). This longitudinal aperture facilitates advancement of the tapered flexible extension 411 along an insertion wire (not shown). The longitudinal aperture also provides a channel for the introduction of medical reagents. For example, it may be desirable to supply a contrast agent to allow angiography to be performed during placement and deployment phases of the medical procedure.

A thin-walled metal tube 415 is fastened to the extension 411. The thin-walled metal tube 415 is flexible so that the introducer 400 can be advanced along a relatively tortuous vessel, such as a femoral artery, and so that the distal attachment region 482 can be longitudinally and rotationally manipulated. The thin-walled metal tube 415 extends through the introducer 400 to the manipulation section 480, terminating at a connection means 416.

The connection means 416 is adapted to accept a syringe to facilitate the introduction of reagents into the thin-walled metal tube 415. The thin-walled metal tube 415 is in fluid communication with the apertures 412 of the flexible extension 411. Therefore, reagents introduced into connection means 416 will flow to and emanate from the apertures 412.

A plastic tube 441 is coaxial with and radially outside of the thin-walled metal tube 415. The plastic tube 441 is "thick-walled"—its wall is preferably several times thicker than that of the thin-walled metal tube 415. A sheath 430 is coaxial with and radially outside of the plastic tube 441. The thick-walled plastic tube 441 and the sheath 430 extend distally to the manipulation region 480.

During the placement phase of the medical procedure, the prosthesis 420 is retained in a compressed condition by the sheath 430. The sheath 430 extends distally to a gripping and hemostatic sealing means 435 of the external manipulation section 480. During assembly of the introducer 400, the sheath 430 is advanced over the cylindrical sleeve 410 of the proximal attachment region 484 while the prosthesis 420 is held in a compressed state by an external force. A distal attachment (retention) section 440 is coupled to the thick-walled plastic tube 441. The distal attachment section 440 retains a distal end 442 of the prosthesis 420 during the procedure. Likewise, the cylindrical sleeve 410 retains the self-expanding zig-zag stent 421.

The distal end 442 of the prosthesis 420 is retained by the distal attachment section 440. The distal end 442 of the prosthesis 420 has a loop (not shown) through which a distal trigger wire (not shown) extends. The distal trigger wire extends through an aperture (not shown) in the distal attachment section 440 into an annular region between the thin-walled tube 415 and the thick-walled tube 441. The distal trigger wire extends through the annular space to the manipulation region 480. The distal trigger wire exits the annular space at a distal wire release mechanism 425.

The external manipulation section 480 includes a hemostatic sealing means 435. The hemostatic sealing means 435 includes a hemostatic seal (not shown) and a side tube 429. The hemostatic sealing means 435 also includes a clamping collar (not shown) that clamps the sheath 430 to the hemostatic seal, and a silicone seal ring (not shown) that forms a hemostatic seal around the thick-walled plastic tube 441. The side tube 429 facilitates the introduction of medical reagents between the thick-walled tube 441 and the sheath 430.

A proximal portion of the external manipulation section 480 includes a release wire actuation section that has a body 436. The body 436 is mounted onto the thick-walled plastic tube 441. The thin-walled tube 415 passes through the body 436. The distal wire release mechanism 425 and the proximal wire release mechanism 424 are mounted for slidable movement onto the body 436.

The positioning of the proximal and distal wire release mechanisms 424 and 425 is such that the proximal wire release mechanism 424 must be moved before the distal wire release mechanism 425 can be moved. Therefore, the distal end 442 of the prosthesis 420 cannot be released until the self-expanding zig-zag stent 421 has been released, and the barbs 451 have been anchored to the lumen. Clamping screws 437 prevent inadvertent early release of the prosthesis 420. A hemostatic seal (not shown) is included so that the release wires can extend out through the body 436 without unnecessary blood loss during the medical procedure.

A distal portion of the external manipulation section 480 includes a pin vise 439. The pin vise 439 is mounted onto the distal end of the body 436. The pin vise 439 has a screw cap 446. When screwed in, vise jaws (not shown) of the pin vise 439 clamp against or engage the thin-walled metal tube 415. When the vise jaws are engaged, the thin-walled tube 415 can only move with the body 436, and hence the thin-walled tube 415 can only move with the thick-walled tube 441. With the screw cap 446 tightened, the entire assembly can be moved together as one piece.

A second introducer may be used to introduce the second prosthetic module 450 and create a tromboning connection. This second introducer may be based on the same principles as the introducer 400 described above, but could be less complex. For example, the second introducer may include a sheath for containing the second prosthetic module 450 in a compressed state, so that it can be introduced into a targeted anatomy and then released to either self-expand or be actively expanded with a balloon.

Deployment

Prosthetic modules are preferably deployed seriatim. The intermodular connection between the second prosthetic module 450 and the bifurcated prosthesis 420 is formed in situ. First the bifurcated prosthesis 420 is deployed, and then the second prosthetic module 450 is deployed. For example, a bifurcated aortic prosthesis 420, as described in WO98/53761, can be deployed into the abdominal aorta. The bifurcated prosthesis 420 has a generally inverted Y-shaped configuration having a body portion 423, a shorter leg 460 and a longer leg 432. The body of the prosthesis is constructed from tubular woven polyester fabric. At the proximal end of the prosthesis 420 is a self-expanding stent 421 which extends beyond the end of the prosthesis and has distally extending barbs 451. The shorter leg 460 and the longer leg 432 have internal projections extending from their distal termini.

This bifurcated prosthesis 420 can be deployed in any method known in the art, preferably the method described in WO98/53761 in which the device is inserted by an introducer via a surgical cut-down into a femoral artery, and then advanced into the desired position over a stiff wire guide using endoluminal interventional techniques. For example, a guide wire (not shown) is first introduced into a femoral artery of the patient and advanced until its tip is beyond the desired deployment region of the prosthesis 420. At this stage, the introducer assembly 400 is fully assembled, and ready for introduction into the patient. The prosthesis 420 is retained at one end by the cylindrical sleeve 410 and the other by the distal attachment sections 440, and compressed by the sheath 430. If an aortic aneurysm is to be repaired, the introducer assembly 400 can be inserted through a femoral artery over the guide wire, and positioned by radiographic techniques, which are not discussed here.

Once the introducer assembly 400 is in the desired deployment position, the sheath 430 is withdrawn to just proximal of the distal attachment section 440. This action releases the middle portion of the prosthesis 420 so that it can expand radially. The proximal self-expanding stent 421, however, is still retained within the cylindrical sleeve 410. Also, the distal end 442 of the prosthesis 420 is still retained within the external sheath 430.

Next, the pin vise 439 is released to allow small movements of the thin-walled tube 415 with respect to the thick-walled tube 441. These movements allow the prosthesis 420 to be lengthened or shortened or rotated or compressed for accurate placement in the desired location within the lumen. Radiopaque markers (not shown) may be placed along the prosthesis 420 to assist with placement of the prosthesis.

When the proximal end of the prosthesis 420 is in place, the proximal trigger wire is withdrawn by distal movement of the proximal wire release mechanism 424. The proximal wire release mechanism 424 and the proximal trigger wire can be completely removed by passing the proximal wire release mechanism 424 over the pin vise 439, the screw cap 446, and the connection means 416.

Next, the screw cap 446 of the pin vise 439 is then loosened. After this loosening, the thin-walled tube 415 can be pushed in a proximal direction to move the cylindrical sleeve 410 in a proximal direction. When the cylindrical sleeve 410 no longer surrounds the self-expanding stent 421, the self-expanding stent 421 expands. When the self-expanding stent 421 expands, the barbs 451 grip the walls of the lumen to hold the proximal end of the prosthesis 420 in place. From this stage on, the proximal end of the prosthesis 420 cannot be moved again.

Once the proximal end of the prosthesis 420 is anchored, the external sheath 430 is withdrawn to distal of the distal attachment section 440. This withdrawal allows the contralateral limb 460 and the longer leg 432 of the prosthesis 420 to expand. At this point, the distal end 442 of the prosthesis 420 may still be moved. Consequently, the prosthesis 420 can still be rotated or lengthened or shortened for accurate positioning. Such positioning of the prosthesis 420 may ensure that the shorter leg 460 extends in the direction of a contralateral artery.

After the shorter leg 460 extends in the direction of the contra-iliac artery, an optional second prosthetic module 450 may be deployed. The second prosthetic module 450 is deployed such that it forms a tromboning connection with the shorter leg 460 and extends from the shorter leg 460 into the contralateral artery.

The method of introduction of the second prosthetic module 450 is as follows. A guide wire (not shown) is introduced into the contralateral femoral artery and advanced until its tip is above the region into which the prosthesis is to be deployed. The second introducer is then advanced over the guide wire with an oscillating and rotating action until the extension prosthesis is overlapped one full stent within the contralateral limb 460. A final position check may then be made before the sheath is withdrawn while holding the thick-walled tube in place.

The introducer and deployment method described above can be adapted for implantation in other regions. For example, if a first prosthetic module is placed into the aorta, a connecting prosthetic module can be placed into the renal, iliac, superior mesenteric, celiac or other artery to form a tromboning interconnection. If a first prosthetic module is placed into the thoracic aorta, a connecting prosthetic module can be placed into another portion of the thoracic aorta, the left subclavian, left common carotid, innominate or other artery. Furthermore, prosthetic modules which are implanted in the same artery can be connected to each other. The overlap region of each of these embodiments is preferably adapted to the size of the relevant anatomy and the forces to which the prostheses are exposed in the relevant anatomy.

Other features and aspects of this invention will be appreciated by those skilled in the art upon reading and understanding this specification. Such features, aspects and expected variations and modifications are clearly within the scope of this invention.

EXAMPLE 1

Thirty feet of whole intestine from a mature adult hog is rinsed with water. This material is then treated in a 0.2% by volume peracetic acid in a 5% by volume aqueous ethanol solution for a period of two hours with agitation. The tela submucosa layer is then delaminated in a disinfected casing machine from the whole intestine. The delaminated tela submucosa is rinsed four (4) times with sterile water and tested for impurities or contaminants such as endotoxins, microbial organisms, and pyrogens. The resultant tissue was found to have essentially zero bioburden level. The tela submucosa layer separated easily and consistently from the whole intestine and was found to have minimal tissue debris on its surface.

EXAMPLE 2

A ten foot section of porcine whole intestine is washed with water. After rinsing, this section of tela submucosa intestinal source material is treated for about two and a half hours in 0.2% peracetic acid by volume in a 5% by volume aqueous ethanol solution with agitation. Following the treatment with peracetic acid, the tela submucosa layer is delaminated from the whole intestine. The resultant tela submucosa is then rinsed four (4) times with sterile water. The bioburden was found to be essentially zero.

EXAMPLE 3

A small section of the tela submucosa intestinal material was subcutaneously implanted in a rat. Within 72 hours, significant angiogenesis was observed.

EXAMPLE 4

Two sections of small intestine are processed by different methods. The first section is rinsed in tap water, disinfected for 2 hours in a 5% by volume aqueous ethanol solution comprising 0.2% by volume peracetic acid, pH approximately 2.6, delaminated to the tela submucosa, rinsed in purified water, divided into two samples and rapidly frozen. The second section is rinsed in tap water, delaminated to the tela submucosa, rinsed in purified water, placed in a 10% neomycin sulfate solution for 20 minutes (as described in U.S. Pat. No. 4,902,508), rinsed in purified water, divided into two samples and rapidly frozen. The four above-prepared samples are tested for bioburden and endotoxin levels. The first two samples each have bioburdens of less than 0.1 CFU/g and endotoxin levels of less than 0.1 EU/g. The second two samples have respective bioburdens of 1.7 CFU/g and 2.7 CFU/g and respective endotoxin levels of 23.9 EU/g and 15.7 EU/g.

EXAMPLE 5

Three sections of small intestine are processed by different methods. The first is rinsed in tap water, disinfected for 2 hours in a 5% by volume aqueous ethanol solution comprising 0.2% by volume peracetic acid, pH about 2.6, delaminated to the tela submucosa, rinsed in purified water, and rapidly frozen. The second is rinsed in tap water, delaminated to the tela submucosa, rinsed in purified water, disinfected according to the methods of Example 1 in U.S. Pat. No. 5,460,962 (treatment for 40 hours in a 0.1% by volume aqueous solution of peracetic acid, buffered to pH 7.2), and rapidly frozen. U.S. Pat. No. 5,460,962 is incorporated herein by reference. The third is rinsed in tap water, delaminated to the tela submucosa, rinsed in purified water, disinfected according to the methods of Example 2 in U.S. Pat. No. 5,460,962 (treatment in 0.1% by volume peracetic acid in high salt solution, buffered to pH 7.2), and rapidly frozen. All three samples were tested for endotoxins. The endotoxin levels were <0.14 EU/g for the first sample, >24 EU/g for the second sample, and >28 EU/g for the third sample.

EXAMPLE 6

Two sections of porcine small intestine were infected with $7 \times 10^6$ plaque forming units (PFU) of virus. Both were exposed to a 0.18% peracetic acid, 4.8% aqueous ethanol solution at a nine-to-one weight ratio of solution to material. A first sample was immersed in this solution for 5 minutes; the second was immersed for 2 hours. The material processed for 5 minutes exhibited 400 PFU per gram of material. The material processed for 2 hours exhibited zero PFU per gram of material.

EXAMPLE 7

Purified tela submucosa, prepared as described herein, was tested to determine its nucleic acid content. Four samples of material weighing 5 mg each were subjected to DNA/RNA extraction as detailed in the DNA/RNA Isolation Kit (Amersham Lifescience Inc., Arlington Heights, Ill.). Nucleic acid quantitation was performed by spectrophotometric determination of solution optical densities at 260 nm and 280 nm. The average nucleic acid content was 1.9±0.2 µg per milligram of material.

Small intestine submucosa, prepared as described in U.S. Pat. No. 4,902,508, was tested to determine its nucleic acid content. Four samples of material weighing 5 mg each were subjected to DNA/RNA extraction as detailed in the DNA/RNA Isolation Kit by Amersham. Nucleic acid quantitation was performed by spectrophotometric determination of solution optical densities at 260 nm and 280 nm. The average nucleic acid content was 2.4±0.2 µg per milligram of material.

EXAMPLE 8

Sections of tela submucosa prepared according to the methods described herein were sent to an independent testing laboratory (NamSA, Inc., Northwood, Ohio) for biocompatibility testing as described in the standard ISO 10993. The samples were tested for USP Acute Systemic Toxicity, USP Intracutaneous Toxicity, Cytotoxicity, LAL Endotoxin, material-mediated Pyrogenicity, Direct Contact Hemolysis, and Primary Skin Irritation. The samples passed all tests, indicating that the material is biocompatible.

The invention claimed is:

1. An endoluminal device comprising:
    a stent;
    a first tubular graft supported by the stent, the first tubular graft comprising a proximal opening, a distal opening, and a synthetic material; and
    a tubular bioremodelable material having two open ends, wherein the tubular bioremodelable material extends the length of the first tubular graft beyond at least one of the proximal and distal openings of the first tubular graft.

2. The endoluminal device of claim 1, wherein the tubular bioremodelable material comprises one of an extracellular matrix material and a synthetic matrix material.

3. The endoluminal device of claim 2, wherein the extracellular matrix material comprises purified small intestine submucosa.

4. The endoluminal device of claim 1, wherein one of the open ends of the tubular bioremodelable material is affixed to the one of the proximal or distal openings of the first tubular graft.

5. The endoluminal device of claim 4, wherein the tubular bioremodelable material is affixed by suturing, stitching, gluing, or stapling.

6. The endoluminal device of claim 4, further comprising a second tubular graft supported by another stent and having an open end, the second tubular graft comprising a synthetic material, wherein the open end of the second tubular graft is affixed to the other open end of the tubular bioremodelable graft material so that the tubular bioremodelable material connects the first tubular graft with the second tubular graft.

7. The endoluminal device of claim 6, wherein the second tubular graft is affixed by suturing, stitching, gluing, or stapling.

8. The endoluminal device of claim 2, wherein the stent is at least partially coated with the extracellular matrix material.

9. An endoluminal device comprising:
a first prosthetic module having an opening at one end;
a second prosthetic module having an opening at one end; and
a tubular bioremodelable module having two open ends, wherein the tubular bioremodelable material connects the opening of the first prosthetic module with the opening of the second prosthetic module.

10. The endoluminal device of claim 9, wherein the tubular bioremodelable material comprises one of an extracellular matrix material and a synthetic matrix material.

11. The endoluminal device of claim 9, wherein the extracellular matrix material comprises purified small intestine submucosa.

12. An endoluminal device comprising:
a stent;
a tubular graft supported by the stent, the tubular graft comprising
a proximal opening,
a distal opening,
at least one other opening disposed in the tubular graft between the proximal and the distal openings, and
a synthetic material; and
a bioremodelable material associated with an exterior surface of the tubular graft in at least one band adjacent the other opening disposed in the tubular graft.

13. The endoluminal device of claim 12, wherein the bioremodelable material comprises one of an extracellular matrix material and a synthetic matrix material.

14. The endoluminal device of claim 12, wherein the extracellular matrix material comprises purified small intestine submucosa.

15. The endoluminal device of claim 13, wherein the extracellular matrix material comprises at least one filament of purified small intestine submucosa.

16. The endoluminal device of claim 15, wherein the at least one filament of purified small intestine submucosa is associated with the graft by one of weaving, knitting, and sewing.

17. The endoluminal device of claim 13, wherein the extracellular matrix material comprises a purified small intestine submucosa particulate associated with the graft by a process selected from a group consisting of impregnating in the synthetic material and coating on the synthetic material.

18. The endovascular device of claim 13, wherein the extracellular matrix material comprises at least one sheet of purified small intestine submucosa that is affixed to the exterior surface of the tubular graft.

19. The endovascular device of claim 18, wherein the at least one sheet of purified small intestine submucosa is associated with the graft by affixing with one of adhesive, staples, and sutures.

20. The endovascular device of claim 13, wherein the extracellular matrix material is impregnated into the synthetic material with the assistance of a partial vacuum.

* * * * *